United States Patent
Bothorel et al.

(10) Patent No.: US 11,154,260 B2
(45) Date of Patent: Oct. 26, 2021

(54) APPARATUS FOR PARTIAL CT IMAGING COMPRISING A COLLIMATOR TO CENTER A RADIATION BEAM TOWARD A REGION OF INTEREST SPACED APART FROM A ROTATION AXIS

(71) Applicant: TROPHY, Croissy-Beaubourg (FR)

(72) Inventors: Sylvie M. Bothorel, Paris (FR); Vincent Loustauneau, Fontenay Sous Bois (FR); Colombe Maury, Ozoir la Ferrière (FR); Jean-Marc Inglese, Bussy Saint Georges (FR)

(73) Assignee: TROPHY, Croissy-Beaubourg (FR)

( * ) Notice: Subject to any disclaimer, the term of this patent is extended or adjusted under 35 U.S.C. 154(b) by 214 days.

(21) Appl. No.: 14/424,210

(22) PCT Filed: Mar. 15, 2013

(86) PCT No.: PCT/IB2013/000952
§ 371 (c)(1),
(2) Date: Feb. 26, 2015

(87) PCT Pub. No.: WO2014/037770
PCT Pub. Date: Mar. 13, 2014

(65) Prior Publication Data
US 2015/0297158 A1    Oct. 22, 2015

Related U.S. Application Data

(60) Provisional application No. 61/698,061, filed on Sep. 7, 2012, provisional application No. 61/736,025, filed on Dec. 12, 2012.

(51) Int. Cl.
*A61B 6/03*       (2006.01)
*A61B 6/06*       (2006.01)
(Continued)

(52) U.S. Cl.
CPC .................. *A61B 6/14* (2013.01); *A61B 6/032* (2013.01); *A61B 6/035* (2013.01); *A61B 6/06* (2013.01);
(Continued)

(58) Field of Classification Search
CPC ........... A61B 6/032; A61B 6/035; A61B 6/06; A61B 6/14; A61B 6/4435; A61B 6/4441; A61B 6/469; A61B 6/4429
(Continued)

(56) References Cited

U.S. PATENT DOCUMENTS 4,817,119 A * 3/1989 Ledley .................. A61B 6/032
378/19
5,090,037 A * 2/1992 Toth ........................ G21K 1/025
378/14
(Continued)

FOREIGN PATENT DOCUMENTS

EP    2 364 648 A1    9/2011
JP    H09122118 A    5/1997
(Continued)

OTHER PUBLICATIONS

International Search Report, International application No. PCT/IB2013/000952, dated Mar. 9, 2013, 3 pages.
(Continued)

*Primary Examiner* — Allen C. Ho

(57) ABSTRACT

An apparatus for computed tomography imaging of a patient has a rotatable mount that is actuable to rotate about a rotation axis and that supports, at opposite ends an x-ray source and an x-ray detector, wherein the x-ray source is disposed to direct a radiation beam through the patient and toward the detector. A patient positioning apparatus positions the patient relative to the rotation axis. A control logic processor controls rotation of the rotatable mount and
(Continued)

acquires image data for the patient at each of a number of angular positions about the rotation axis. A collimator is disposed in front of the x-ray source and controlled by the control logic processor to center the radiation beam, at each of the plurality of angular positions, on a region of interest that is spaced apart from the rotation axis.

6 Claims, 27 Drawing Sheets

(51) Int. Cl.
*A61B 6/14* (2006.01)
*A61B 6/00* (2006.01)
*G06T 11/00* (2006.01)
*G06T 15/08* (2011.01)

(52) U.S. Cl.
CPC .......... *A61B 6/4085* (2013.01); *A61B 6/4429* (2013.01); *A61B 6/4435* (2013.01); *A61B 6/469* (2013.01); *A61B 6/547* (2013.01); *G06T 11/003* (2013.01); *G06T 15/08* (2013.01); *A61B 6/4441* (2013.01); *F04C 2270/041* (2013.01); *G06T 2211/40* (2013.01)

(58) Field of Classification Search
USPC .............................. 378/38–40, 150–153, 19
See application file for complete search history.

(56) References Cited

U.S. PATENT DOCUMENTS

| | | | | |
|---|---|---|---|---|
| 5,224,136 A * | 6/1993 | Toth | ........................ | G21K 1/04 378/14 |
| 5,550,886 A * | 8/1996 | Dobbs | .................... | A61B 6/032 378/19 |
| 5,768,331 A * | 6/1998 | Gordon | .................. | A61B 6/032 378/19 |
| 6,018,563 A * | 1/2000 | Arai | ........................ | A61B 6/14 378/39 |
| 6,118,842 A * | 9/2000 | Arai | ........................ | A61B 6/032 378/38 |
| 6,282,264 B1 * | 8/2001 | Smith | .................. | A61B 6/0457 378/167 |
| 6,289,074 B1 * | 9/2001 | Arai | ........................ | A61B 6/032 378/38 |
| 6,463,122 B1 * | 10/2002 | Moore | .................. | A61B 6/0435 378/17 |
| 6,493,415 B1 * | 12/2002 | Arai | ........................ | A61B 6/14 378/38 |
| 6,496,558 B2 * | 12/2002 | Graumann | ........... | A61B 6/0478 378/197 |
| 6,501,828 B1 * | 12/2002 | Popescu | .................. | A61B 6/06 378/145 |
| 6,619,839 B2 * | 9/2003 | Yoshimura | ............ | A61B 6/0478 378/195 |
| 6,707,876 B2 * | 3/2004 | Tanigawa | ................ | A61B 6/032 378/19 |
| 6,851,851 B2 * | 2/2005 | Smith | .................. | A61B 6/0457 378/167 |
| 6,940,941 B2 * | 9/2005 | Gregerson | ............. | A61B 6/032 250/363.05 |
| 6,990,175 B2 * | 1/2006 | Nakashima | ............ | A61B 6/032 378/101 |
| 7,001,045 B2 * | 2/2006 | Gregerson | ............. | A61B 6/035 362/253 |
| 7,039,156 B2 * | 5/2006 | Arai | ..................... | A61B 6/0478 378/22 |
| 7,085,343 B2 * | 8/2006 | Shinno | ................... | A61B 6/032 378/19 |
| 7,108,421 B2 * | 9/2006 | Gregerson | ............. | A61B 6/032 378/146 |
| 7,110,487 B2 * | 9/2006 | Baba | ...................... | A61B 6/466 378/11 |
| 7,113,569 B2 * | 9/2006 | Okumura | ............... | A61B 6/032 378/150 |
| 7,187,749 B2 * | 3/2007 | Suzuki | ................. | A61B 6/0478 378/162 |
| 7,188,998 B2 * | 3/2007 | Gregerson | ............... | A61B 6/02 378/197 |
| 7,197,107 B2 * | 3/2007 | Arai | ....................... | A61B 6/032 378/15 |
| 7,197,109 B2 * | 3/2007 | Rotondo | .................. | A61B 6/14 378/196 |
| 7,298,814 B2 * | 11/2007 | Popescu | .................. | A61B 6/032 378/19 |
| 7,322,746 B2 * | 1/2008 | Beckhaus | .............. | A61B 6/032 378/19 |
| 7,336,763 B2 * | 2/2008 | Spartiotis | ................. | A61B 6/14 378/38 |
| 7,347,622 B2 * | 3/2008 | Sadakane | ............... | A61B 6/032 378/197 |
| 7,418,074 B2 * | 8/2008 | Du | ........................ | A61B 6/032 378/13 |
| 7,421,059 B2 * | 9/2008 | Suzuki | ..................... | A61B 6/04 378/38 |
| 7,486,759 B2 * | 2/2009 | Suzuki | ..................... | A61B 6/14 378/38 |
| 7,486,767 B2 * | 2/2009 | Sonobe | .................. | A61B 6/105 378/191 |
| 7,534,038 B2 * | 5/2009 | Rotondo | .................. | A61B 6/08 378/205 |
| 7,577,232 B2 * | 8/2009 | Tachibana | ................ | A61B 6/14 378/116 |
| 7,688,941 B2 * | 3/2010 | Thoms | ..................... | A61B 6/04 378/195 |
| 7,711,085 B2 * | 5/2010 | Suzuki | ..................... | A61B 6/14 378/39 |
| 7,720,191 B2 * | 5/2010 | Muller | ................. | A61B 6/5235 378/197 |
| 7,742,560 B2 * | 6/2010 | Spartiotis | ................. | A61B 6/14 250/370.09 |
| 7,773,720 B2 * | 8/2010 | Honjo | .................... | A61B 6/032 378/189 |
| 7,787,586 B2 * | 8/2010 | Yoshimura | ............. | A61B 6/032 378/38 |
| 7,798,708 B2 * | 9/2010 | Erhardt | .................. | A61B 6/032 250/370.09 |
| 7,852,981 B2 * | 12/2010 | Luo | ........................ | A61B 6/032 250/370.09 |
| 7,945,016 B2 * | 5/2011 | Bothorel | ................. | A61B 6/14 378/148 |
| 7,978,813 B2 * | 7/2011 | Yoshimura | ............... | A61B 6/14 378/38 |
| 7,991,107 B2 * | 8/2011 | Sadakane | ............... | A61B 6/14 378/39 |
| 7,995,704 B2 * | 8/2011 | Ro | ......................... | A61B 6/14 378/197 |
| 8,005,186 B2 * | 8/2011 | Lee | ........................ | A61B 6/032 378/13 |
| 8,005,187 B2 * | 8/2011 | Suzuki | .................. | A61B 6/032 378/19 |
| 8,009,794 B2 * | 8/2011 | Partain | ................... | A61B 6/032 378/150 |
| 8,050,381 B2 * | 11/2011 | Mori | ....................... | A61B 6/14 378/191 |
| 8,064,569 B2 * | 11/2011 | Arai | ....................... | A61B 6/032 378/108 |
| 8,147,139 B2 * | 4/2012 | Papaioannou | ........... | A61B 6/04 378/195 |
| 8,184,775 B1 * | 5/2012 | Fan | ...................... | A61B 6/4085 378/147 |
| 8,213,569 B2 * | 7/2012 | Zaiki | ..................... | A61B 6/035 378/147 |
| 8,254,520 B2 * | 8/2012 | Sadakane | ............... | A61B 6/032 378/19 |
| 8,290,119 B2 * | 10/2012 | Tancredi | .................. | A61B 6/14 378/197 |

(56) References Cited

U.S. PATENT DOCUMENTS

| | | | | |
|---|---|---|---|---|
| 8,300,762 B2 * | 10/2012 | Suzuki | A61B 6/032 378/15 |
| 8,363,780 B2 * | 1/2013 | Loustauneau | A61B 6/587 378/13 |
| 8,396,184 B2 * | 3/2013 | Shinno | A61B 6/032 378/5 |
| 8,396,186 B2 * | 3/2013 | Tomoe | A61B 6/14 378/39 |
| 8,401,267 B2 * | 3/2013 | Nakai | A61B 6/032 382/132 |
| 8,430,565 B2 * | 4/2013 | Vartiainen | A61B 6/04 378/208 |
| 8,433,033 B2 * | 4/2013 | Harata | A61B 6/14 378/38 |
| 8,451,972 B2 * | 5/2013 | Dafni | A61B 6/032 378/11 |
| 8,483,352 B2 * | 7/2013 | Hoffman | A61B 6/032 378/19 |
| 8,483,353 B2 * | 7/2013 | Hoffman | A61B 6/032 378/19 |
| 8,488,736 B2 * | 7/2013 | Hoffman | A61B 6/032 378/19 |
| 8,498,375 B2 * | 7/2013 | Suzuki | A61B 6/032 378/39 |
| 8,503,603 B2 * | 8/2013 | Tancredi | A61B 6/0478 378/39 |
| 8,503,604 B2 * | 8/2013 | Inglese | A61B 6/14 378/19 |
| 8,515,007 B2 * | 8/2013 | Kantor | A61B 6/14 378/39 |
| 8,538,110 B2 * | 9/2013 | Nakai | A61B 6/032 382/131 |
| 8,559,596 B2 * | 10/2013 | Thomson | G06T 7/0014 378/65 |
| 8,571,172 B2 * | 10/2013 | Dafni | A61B 6/032 378/11 |
| 8,588,364 B2 * | 11/2013 | Suzuki | A61B 6/14 378/38 |
| 8,594,406 B2 * | 11/2013 | Virmani | A61B 5/4872 382/131 |
| 8,750,450 B2 * | 6/2014 | Ulrici | A61B 6/14 378/38 |
| 8,768,029 B2 * | 7/2014 | Helm | A61B 6/4476 378/20 |
| 8,768,032 B2 * | 7/2014 | Basu | G06T 11/005 250/559.05 |
| 8,817,944 B2 * | 8/2014 | Arai | A61B 6/06 378/11 |
| 8,855,262 B2 * | 10/2014 | Takemoto | A61B 6/02 378/197 |
| 8,979,366 B2 * | 3/2015 | Tomoe | A61B 6/027 378/197 |
| 8,988,517 B2 * | 3/2015 | Mori | A61B 6/032 348/77 |
| 9,036,775 B2 * | 5/2015 | Yoshikawa | A61B 6/145 378/38 |
| 9,036,776 B2 * | 5/2015 | Sadakane | A61B 6/145 378/38 |
| 9,044,187 B2 * | 6/2015 | Koehler | A61B 6/032 |
| 9,084,568 B2 * | 7/2015 | Katsumata | A61B 6/14 |
| 9,113,799 B2 * | 8/2015 | Katsumata | A61B 6/032 |
| 9,119,575 B2 * | 9/2015 | Sadakane | A61B 6/03 |
| 9,125,572 B2 * | 9/2015 | Noo | A61B 6/027 |
| 9,198,626 B2 * | 12/2015 | Heuscher | A61B 6/032 |
| 9,200,948 B2 * | 12/2015 | Jan | A61B 6/035 |
| 9,237,874 B2 * | 1/2016 | DeMan | A61B 6/032 |
| 9,259,191 B2 * | 2/2016 | Noo | G21K 1/02 |
| 9,275,189 B2 * | 3/2016 | Walker | A61B 6/032 |
| 9,295,434 B2 * | 3/2016 | Herold | A61B 6/032 |
| 9,307,946 B2 * | 4/2016 | Cowdery | A61B 6/14 |
| 9,357,971 B2 * | 6/2016 | Yoshikawa | A61B 6/032 |
| 9,375,192 B2 * | 6/2016 | Schildkraut | A61B 6/032 |
| 9,380,984 B2 * | 7/2016 | Li | A61B 6/032 |
| 9,389,320 B2 | 7/2016 | Ogawa et al. | |
| 9,408,579 B2 * | 8/2016 | Yamakawa | A61B 6/14 |
| 9,417,340 B2 * | 8/2016 | Basu | G01T 1/2985 |
| 9,420,976 B2 * | 8/2016 | Jackson | A61B 6/06 |
| 9,480,453 B2 * | 11/2016 | Yamanaka | A61B 6/035 |
| 9,510,795 B2 * | 12/2016 | Takemoto | A61B 6/14 |
| 9,597,041 B2 * | 3/2017 | Claus | A61B 6/032 |
| 9,636,076 B2 * | 5/2017 | Fujisawa | A61B 6/5217 |
| 9,655,584 B2 * | 5/2017 | Lee | A61B 6/542 |
| 9,668,705 B2 * | 6/2017 | Yamakawa | A61B 6/14 |
| 2003/0076920 A1 | 4/2003 | Shinno et al. | |
| 2004/0202283 A1 | 10/2004 | Okumura et al. | |

FOREIGN PATENT DOCUMENTS

| | | | |
|---|---|---|---|
| JP | 20041809715 A | 7/2004 | |
| JP | 2007029168 | 2/2007 | |
| JP | 2007-135658 A | 6/2007 | |
| JP | WO2009/133896 A1 * | 11/2009 | A61B 6/032 |
| JP | 2011-041598 A | 3/2011 | |
| JP | 2013-135842 A | 7/2013 | |
| WO | WO 2012086648 | 6/2012 | |

OTHER PUBLICATIONS

Japanese Office Action dated Oct. 24, 2017 from JP Patent Application No. 2015-530500; pp. 1-6, translation attached.

* cited by examiner

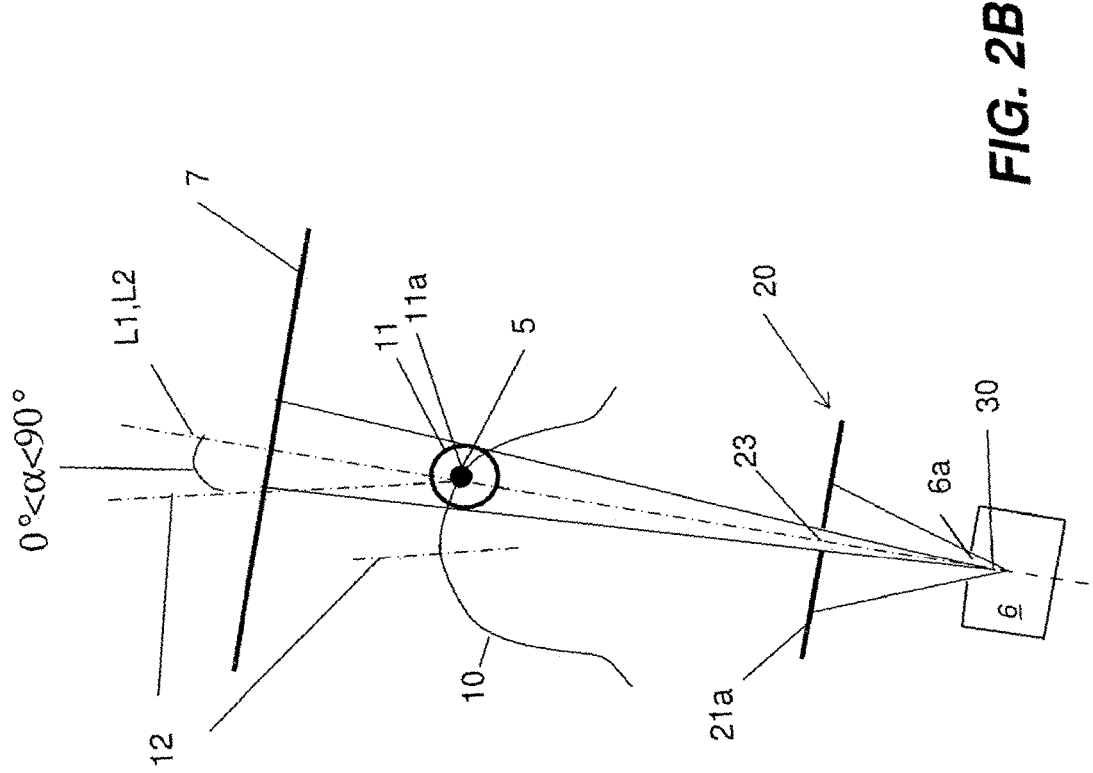

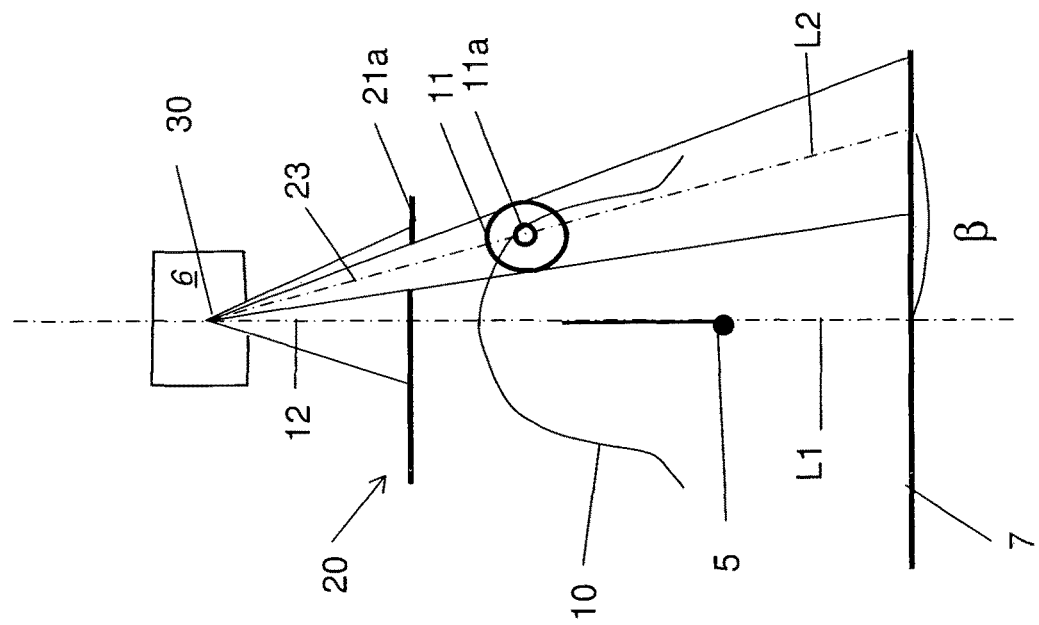

APPARATUS FOR PARTIAL CT IMAGING COMPRISING A COLLIMATOR TO CENTER A RADIATION BEAM TOWARD A REGION OF INTEREST SPACED APART FROM A ROTATION AXIS

CROSS REFERENCE TO RELATED APPLICATIONS

This application claims the benefit of and is a U.S. National Phase filing of PCT Application PCT/IB13/00952 filed Mar. 15, 2013 entitled "APPARATUS FOR PARTIAL CT IMAGING", in the name of Bothorel et al., which claims the benefit of U.S. Provisional Patent application No. 61/698,061, filed on Sep. 7, 2012, entitled: "APPARATUS FOR PARTIAL CT IMAGING", in the name of Bothorel et al., and which claims the benefit of U.S. Provisional Patent application No. 61/736,025, filed on Dec. 12, 2012, entitled: "APPARATUS FOR PARTIAL CT IMAGING", in the name of Bothorel et al., and is incorporated herein in its entirety.

FIELD OF THE INVENTION

The present invention relates generally to the field of volumetric imaging and more particularly to apparatus and methods for obtaining volumetric images of teeth and other structures within the head.

BACKGROUND OF THE INVENTION

A computerized tomography (CT) or cone beam CT (CBCT) imaging apparatus operates by acquiring multiple 2D images with a rotating imaging ensemble or gantry that has an x-ray source and, opposite the x-ray source, an imaging sensor rotating about a fixed axis relative to the patient who is being imaged. CT and CBCT imaging allow the reconstruction of 3D or volume images of anatomical structures of the patient. The resulting volume images are acknowledged to be of particular value for obtaining useful information for assisting diagnosis and treatment. In the context of the present disclosure, the term "CT" is used to include CT systems of various types, including CBCT systems.

There is interest in the use of CT imaging in dental and ear-nose-throat (ENT) applications, as well as for other imaging of the patient's head.

SUMMARY OF THE INVENTION

Embodiments of the present invention address the need for advancing the CT imaging art, particularly for imaging of teeth and other structures of the head. Embodiments of the present invention provide an apparatus for CT imaging that dynamically adjusts the radiation beam, centering the beam apart from the axis of rotation using the collimator assembly, so that, relative to an x-y plane, precision placement of an axis so that it extends through a center of the region of interest is not necessary.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided an apparatus for computed tomography imaging of a patient comprising: a rotatable mount that is actuable to rotate about a rotation axis and that supports, at opposite ends, an x-ray source and a detector, wherein the x-ray source is disposed to direct, at each of a plurality of angular positions of the mount about the rotation axis, a radiation beam through the patient and toward the detector; a patient positioning apparatus for positioning the patient relative to the rotation axis; a control logic processor that controls rotation of the rotatable mount and acquires image data of the patient at each of the plurality of angular positions about the rotation axis; and a collimator disposed in front of the x-ray source and controlled by the control logic processor to center the radiation beam, at each of the plurality of angular positions, on a region of interest that is spaced apart from the rotation axis.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other. Some exaggeration of feature sizes or their geometrical or angular relationships may be useful to show features of the present invention with improved clarity.

FIG. 2B is a top view that shows angular relationships for CT imaging at a second angle, displaced from the first angle of FIG. 2A.

FIGS. 8A-8D are top views that show different angles in an imaging sequence using the adjustable collimator for beam direction according to another alternate embodiment of the present invention.

DETAILED DESCRIPTION OF THE INVENTION

Figure 1:
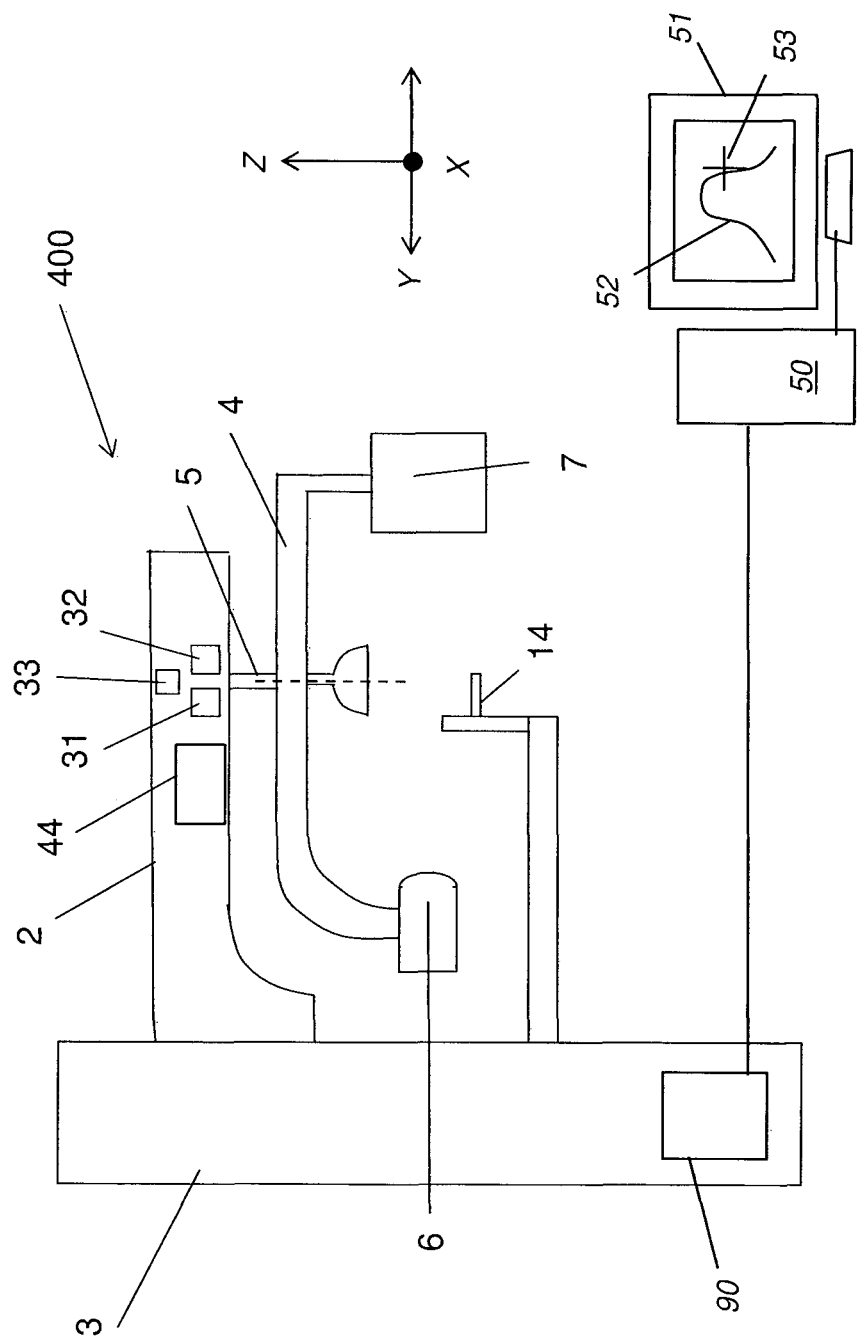
FIG. 1 is a schematic diagram that shows an extra-oral CT dental imaging apparatus.

This application claims priority to two U.S. Provisional patent applications: (1) U.S. Patent Application Ser. No. 61/698,061, filed Sep. 7, 2012 in the names of Sylvie Bothorel et al., entitled APPARATUS FOR PARTIAL CT IMAGING, incorporated herein by reference in its entirety, and (2) U.S. Patent Application Ser. No. 61/736,025, filed Dec. 12, 2012 in the names of Sylvie Bothorel et al., entitled APPARATUS FOR PARTIAL CT IMAGING, incorporated herein by reference in its entirety.

The following is a detailed description of the preferred embodiments of the invention, reference being made to the drawings in which the same reference numerals identify the same elements of structure in each of the several figures.

In the context of the present invention, the terms "digital sensor" and "digital detector" are considered to be equivalent. These describe the panel that obtains image data in a digital radiography system. The term "revolve" has its conventional meaning, to move in a curved path or orbit around a center point.

Where they are used, the terms "first", "second", "third", and so on, do not necessarily denote any ordinal or priority relation, but may be used for more clearly distinguishing one element or time interval from another.

As used herein, the term "energizable" relates to a device or set of components that can be energized to perform an indicated function upon receiving power and, optionally, upon receiving an enabling signal. The term "actuable" has its conventional meaning, relating to a device or component that is capable of effecting an action in response to a stimulus, such as in response to an electrical signal, for example.

Consistent with the present disclosure, lines are substantially in parallel when their directions differ by no more than about 0.5 degree. At angles exceeding this range, lines are considered to be non-parallel.

FIG. 1 shows an embodiment of a CT imaging apparatus 400. A vertical column 3 supports a horizontal arm 2 that adjusts for the patient's height. Horizontal arm 2 supports a mount 4 on an axis 5. Mount 4 supports both an x-ray source 6 and, opposite the x-ray source 6, an x-ray sensor 7. X-ray Source 6 and x-ray sensor 7 are designed to rotate about axis 5, that is, with rotation in the x-y plane. The patient is positioned in line with axis 5 between the x-ray source 6 and the x-ray sensor 7, so that most of the radiation that is directed from x-ray source 6 toward x-ray sensor 7 passes through the patient. The fixed positioning of the patient is made possible by a patient positioning apparatus 14 that is coupled to CT imaging apparatus 400 and may include a chin support, a bite element, temporal holders, ear rods, a forehead support, or a strap for fixing the position of the patient's head, for example. As the mount 4 rotates to each of a number of different angular positions about axis 5, an image of the patient is obtained.

At installation, CT imaging apparatus 400 is calibrated so that axis 5 has a default position in the (x,y) plane corresponding to the vertical location of a given anatomical point of the patient, such as the incisors for example. A control logic processor 90 is in signal communication with a user interface, shown in FIG. 1 as a remote computer 50 with a display 51. The display screen shows a virtual model of a patient arch 52 and a target 53 having the shape of a cross, circle, cross-hairs, or other suitable shape. Using a command that indicates a point of the virtual model of the patient arch 52, the user can displace and re-position target 53. This command is typically entered using a computer mouse or other type of pointer. Target 53 can then be positioned on a location of the patient arch 52 that corresponds to the region of interest of the patient. Once the new position of the target 53 is validated by the user, the target location is sent to control logic processor 90. Control logic Processor 90 then performs the needed computation and, as needed, actuates motors 31, 32 so that axis 5 is positioned at the vertical position of the region of interest of the patient corresponding to the virtual position of the target 53 on patient arch 52 shown on display 51. Alternately, remote computer 50 and its related display 51 are integral with CT imaging apparatus 400, such as part of control logic processor 90.

Figure 2A:
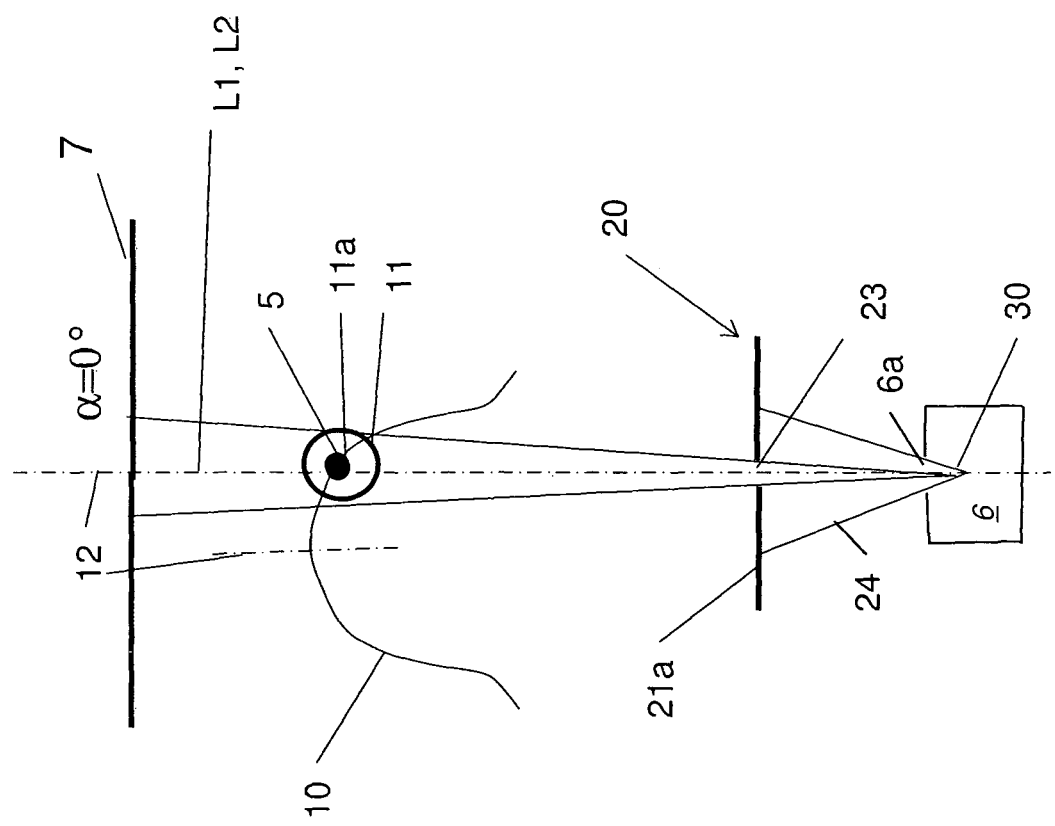
FIG. 2A is a top view that shows angular relationships for CT imaging at a first angle.

FIG. 2A shows, from a schematic top view, parameters and features of the CT scan geometry that relate to the operation of CT imaging apparatus 400 of FIG. 1. For conventional CT scanning, the axis of rotation 5 aligns with, or extends through, the center 11a of a region of interest 11. For dental imaging, region of interest 11 is that portion of a dental arch 10 that is to be scanned. The use of patient positioning apparatus 14 fixes the head of the patient into position for imaging and brings center 11a near axis of rotation 5; however, some additional adjustment is typically required in order to correct the positioning within the x-y plane.

Referring again to FIG. 1, adjustment or horizontal displacement of axis 5 position is performed using X and Y motors 31 and 32 located in horizontal arm 2. Before the beginning of a scan, the axis of rotation 5 is positioned relative to the patient at the vertical position of the center 11a of the region of interest 11 of the patient. A motor 33 in horizontal arm 2 is energized to provide rotation of mount 4 about axis 5. Control logic processor 90, such as a microprocessor or other dedicated logic controller or computer device, is in signal communication with motors 31, 32, 33, and sensing devices and coordinates the operation of CT imaging apparatus 400 components during setup, axis alignment, and scanning. One or more sensor elements 44, in signal communication with control logic processor 90, sense the axial and rotational position of the rotatable mount 4.

As shown in FIG. 1, the patient is positioned at patient positioning apparatus 14, which places the head of the patient at a fixed position between x-ray source 6 and x-ray sensor 7. With the patient in position, the axis of rotation 5 is conveniently horizontally positioned, within the 2-dimensional (2D) x-y plane using motors 31 and 32. CT scanning can then be initiated. Motor 33 is energized and mount 4 rotates about fixed axis 5 to reach successive angular positions, denoted by angle α (FIG. 2A). Angle α indicates the angle between the line L1 and a front-to-rear direction 12 of the patient, termed the anteroposterior direction and shown in a dashed line in FIGS. 2A and 2B.

In FIGS. 2A and 2B, focal spot 30 of the x-ray source 6 is located within a cavity defined by a container of lead or other suitable x-ray absorbing material, provided with an opening, aperture 6a. The beam 24 that passes through aperture 6a is then further limited by collimator 20.

In FIG. 2A, angle α is at 0 degrees. In FIG. 2B, angle α is at some other angle that lies between 0 and 90 degrees. At each of a number of angular positions, x-ray source 6 irradiates the region of interest 11 and a frame of image data is captured. Continuing in this manner, a plurality of frames of the region of interest 11 of the patient are captured at various angular positions α of line L1 relative to the patient.

The angular position α ranges from 0 to 180° for some CT embodiments or from 0-360° for other embodiments. From the plurality of two dimensional frames, control logic processor 90, or other computer that is in signal communication with control logic processor 90 for receiving image data, reconstructs a 3D matrix of grey levels, corresponding to the absorption coefficients of elementary volume elements or voxels of the region of interest 11 that is being radiated.

The schematic views of FIGS. 2A and 2B show two lines L1 and L2 at different angular positions of the scan. Line L1 passes through a focal spot 30 of the x-ray source and the vertical projection of the axis 5. Line L2 indicates the center of the x-ray beam as it is directed through aperture 6a and through an opening 23 provided by a collimator 20. In conventional CT systems, lines L1 and L2 are collinear. This geometric relationship requires that center 11a be aligned with axis 5. This requirement, in turn, requires the use of motors 31 and 32, along with the necessary control logic sequence that is used for repositioning axis 5 in the x-y plane of FIG. 1, depending on the region of interest 11. The x-y plane is the plane of the page for FIGS. 2A and 2B. The region of interest 11 could include, for example, particular teeth of the patient, such as incisors, right or left molars, or other dental structures.

In some cases, the dentist needs information about only a small part of the dental arch 10, for example, for only two or three teeth. In that case, a CT scan with a small field of view is performed, the x-ray beam being tightly collimated by collimator 20 (FIG. 2A). This allows the x-ray sensor 7 to be reduced in size and lower in price and, because it requires only a small size x-ray beam, can help to reduce the overall amount of ionizing radiation to the patient. One drawback with conventional CT apparatus, however, relates to the need for precise 2D positioning of the axis of rotation 5 relative to center 11a, even where only a small portion of the dental arch is to be imaged.

The use of motors 31 and 32 to position axis 5 adds cost and complexity to CT imaging apparatus 400 and adds weight to horizontal arm 2. In addition, extra setup time is needed for readying CT imaging apparatus 400 in preparation to image each patient. Applicants desire to reduce or eliminate one or both of these motors to reduce cost, weight, and complexity of the apparatus and to improve workflow and efficiency in the use of the CT imaging apparatus 400.

Embodiments of the present application are described which reduce/eliminate precise positioning of the axis of rotation 5 relative to the patient and to the center 11a of the region of interest 11. As was shown with respect to FIGS. 1 and 2A, axis of rotation 5 is positioned at the center 11a of the region of interest 11 relative to the x-y plane. Using embodiments of the present application for a CBCT scan, the configuration can differ. Instead, collimator 20 is used to center the radiation beam toward region of interest 11 at each image acquisition angle, that is, with the mount 4 rotated to each angular position, rather than requiring that the radiation beam be centered on axis of rotation 5. According to an embodiment of the present application, axis of rotation 5 lies outside the radiation beam that is emitted from the x-ray source 6 and centered on the region of interest 11 for at least one angular position of x-ray source 6 and x-ray sensor 7 over the range of scan angles.

Figure 3:
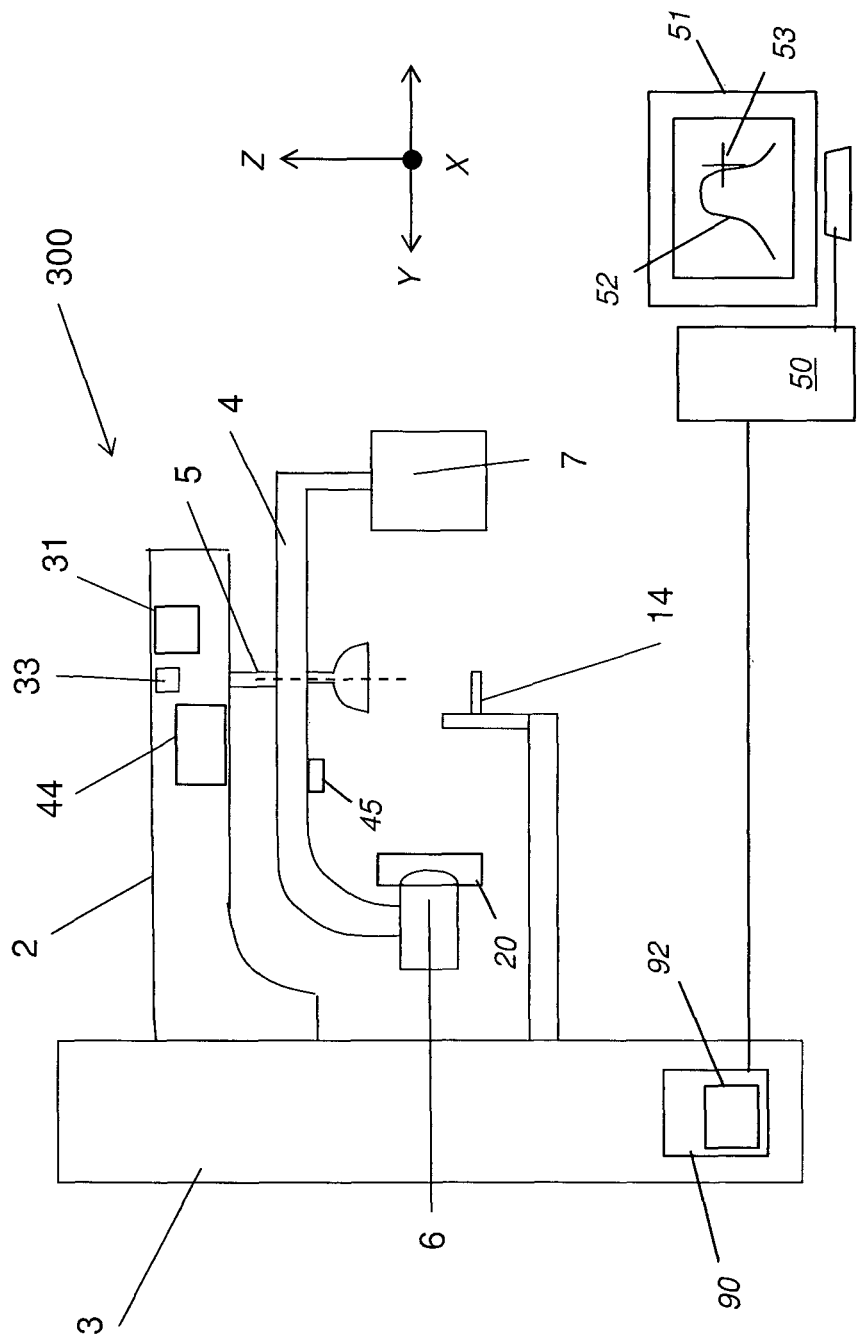
FIG. 3 is a schematic diagram that shows an extra-oral CT dental imaging apparatus according to an embodiment of the present invention.

Referring to FIG. 3, there is shown a CT imaging apparatus 300 that uses a collimator 20 for radiation beam centering. By comparison with FIG. 1, a number of components used in CT imaging apparatus 300 are similar to those used in CT imaging apparatus 400. Notably, motors 31 and 32, while required in the FIG. 1 embodiment, are not required for CT imaging apparatus 300 in FIG. 3. Motor 31 is shown in FIG. 3, but is optional. The axis of rotation (axis 5 in FIGS. 1, 2A, 2B, and 3) is fixed with respect to CT imaging apparatus 300 and to the x-y plane. The patient is positioned at a predetermined location using patient positioning apparatus 14 that is located, relative to the mount 4, so that the vertical projection of axis 5 coincides with a point in the vicinity of the center of the mouth or of the dental arch 10 or other feature of the patient. In general, the center 11a of the region of interest 11 need not coincide with the vertical projection of axis of rotation 5 and may be spaced apart from axis 5, so that axis 5 lies outside the emitted radiation beam for the acquired image at one or more angular positions of mount 4. One or more sensor elements 44, in signal communication with control logic processor 90, sense the rotational position of rotatable mount 4 and, alternately, also sense the relative positions of axis of rotation 5 and patient positioning apparatus 14. Mount 4 can be vertically translated; horizontal arm 2 is movable in a vertical direction along vertical column 3. Control logic processor 90 executes control software 92 for performing mount 4 positioning functions, including rotation, vertical displacement, and positioning of axis of rotation 5. To perform any of these functions, control logic processor 90 accepts operator instructions and, optionally, obtains signals from one or more sensor elements 44 that are part of CT imaging apparatus 300. Methods for sensing and providing movement in a dental imaging apparatus are known to those skilled in the dental apparatus design arts.

Positioning axis of rotation 5 at a known position relative to the patient can be performed in a number of ways. According to an embodiment of the present invention, CT imaging apparatus 300, including patient positioning apparatus 14, is designed so that when the patient is positioned, axis of rotation 5 is in a known relationship with the patient, for example at the vertical position of an area of the patient's mouth. CT imaging apparatus 300 is provided with optional remote computer 50 including display 51 in communication with control logic processor 90. Remote computer 50 can be a remote computer or processor or can be integral with CT imaging apparatus 300. By positioning a target 53 on the patient arch 52 using a computer mouse or other suitable pointer, the user defines region of interest 11 of the patient. This information is then sent to control logic processor 90. Information about the location of region of interest 11 then provides a reference for precise actuation of collimator 20 to aim the radiation beam.

Figure 4A:
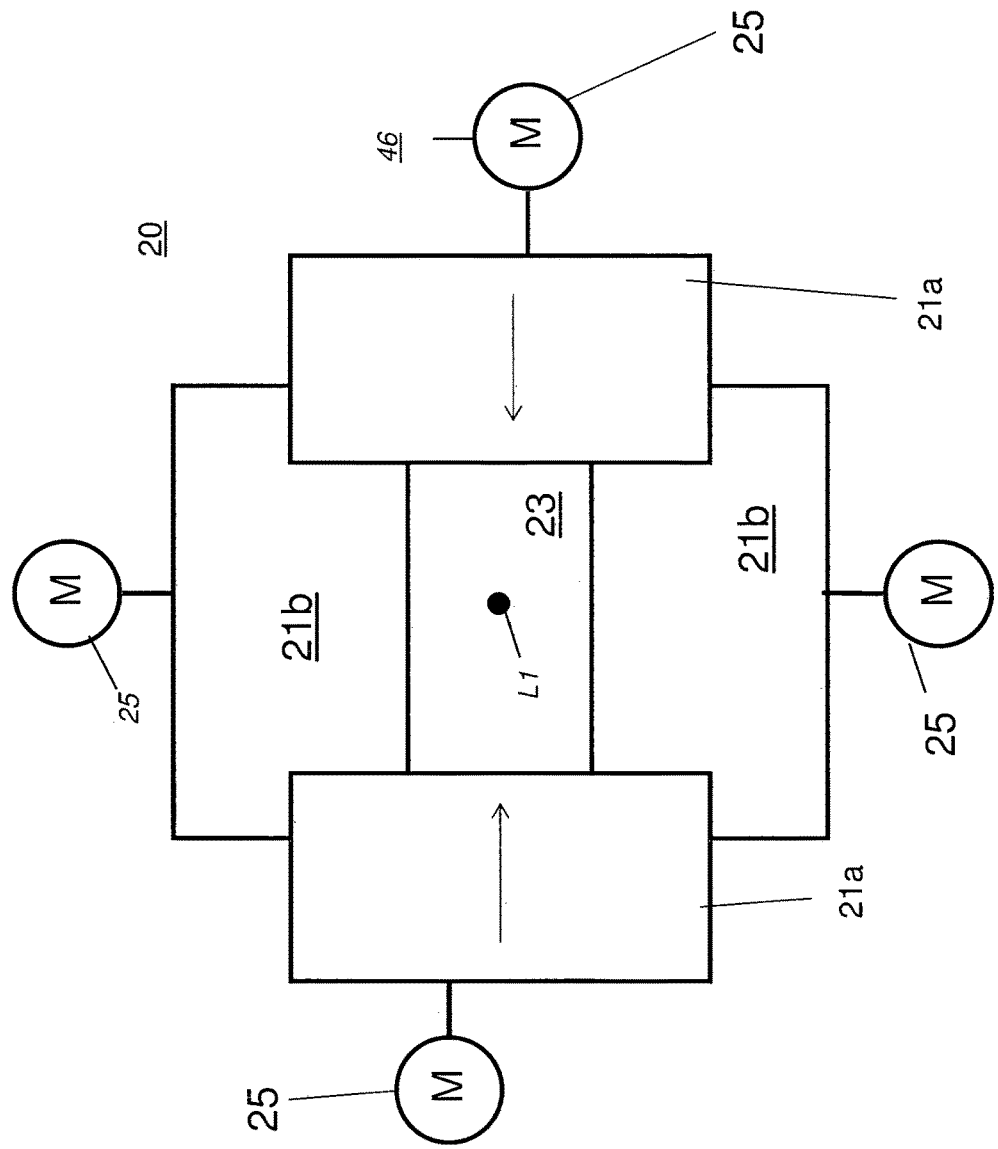
FIG. 4A is a schematic diagram that shows components of a blade collimator for CT imaging.

Collimator 20 serves for beam centering at each angular position according to an embodiment of the present invention. FIG. 4A shows components that form and control collimator 20 according to an embodiment wherein the collimator provides a beam that has a rectangular shape in cross section. Collimator 20 is a blade collimator, provided with paired blades 21a, 21b that are appropriately positioned by motors 25. In conventional practice, the blades 21a, 21b are positioned in such a manner that the center of opening 23 of the collimator 20 is precisely positioned on the straight line L1. In the plan view of FIG. 4A, line L1 extends outwards, normal to the page.

Figure 4B:
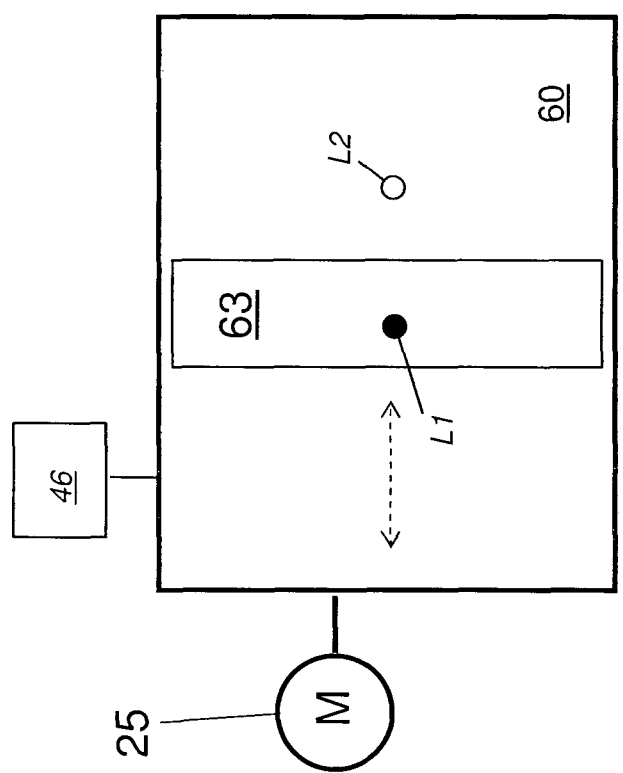
FIG. 4B is a schematic diagram that shows a slit collimator for CT imaging.
Figure 5A:
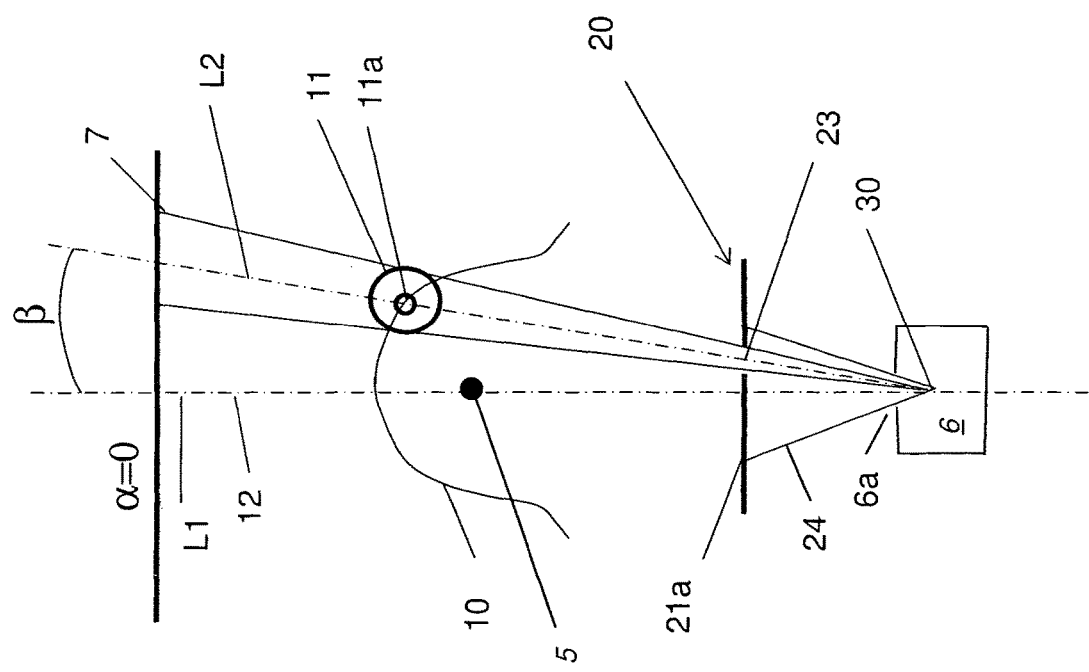
FIGS. 5A-5E show top views illustrating different angles in an imaging sequence using the adjustable collimator for beam direction according to an embodiment of the present invention.
Figure 5B:
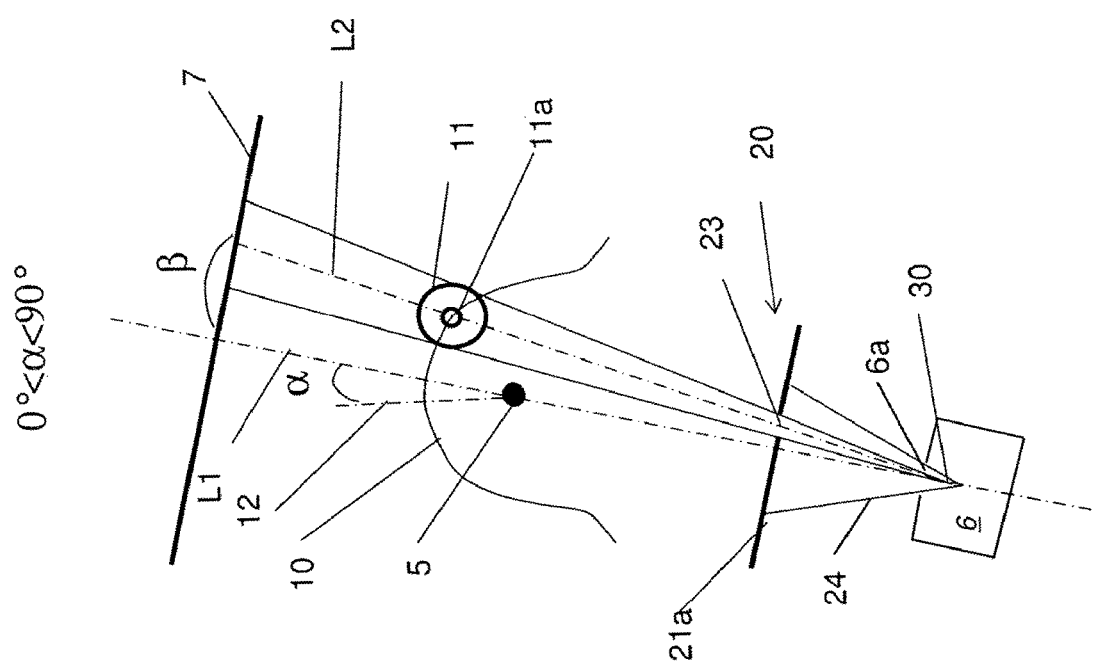
Figure 5C:
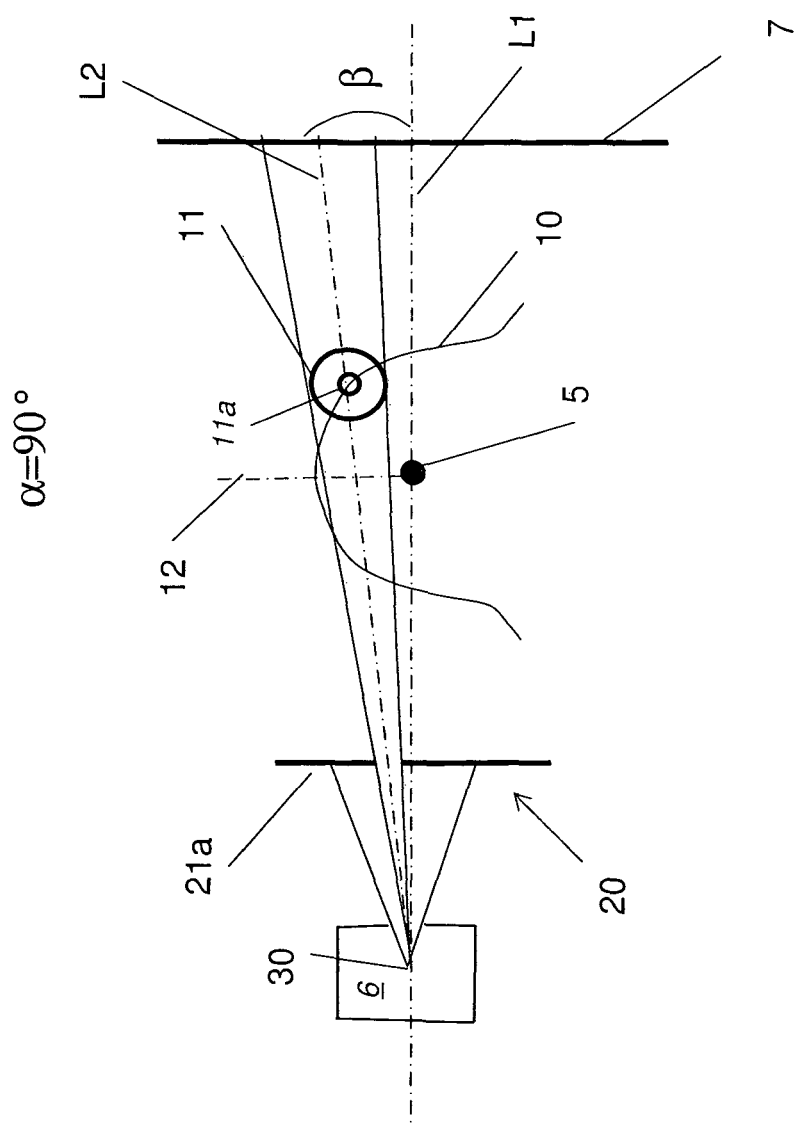
Figure 5D:
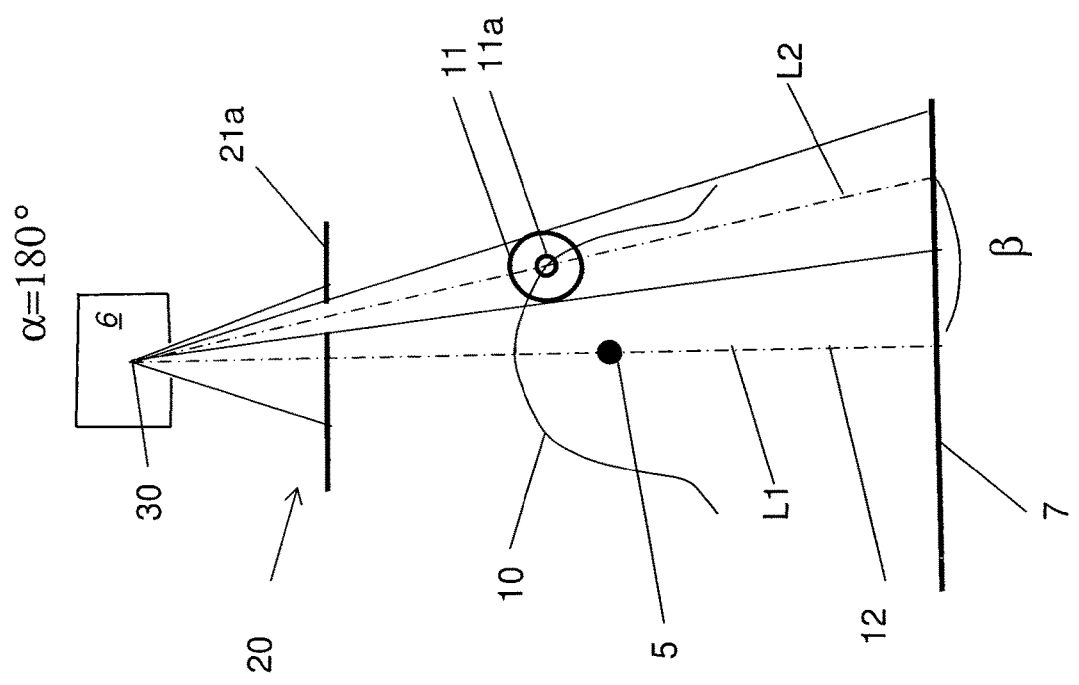
Figure 5E:
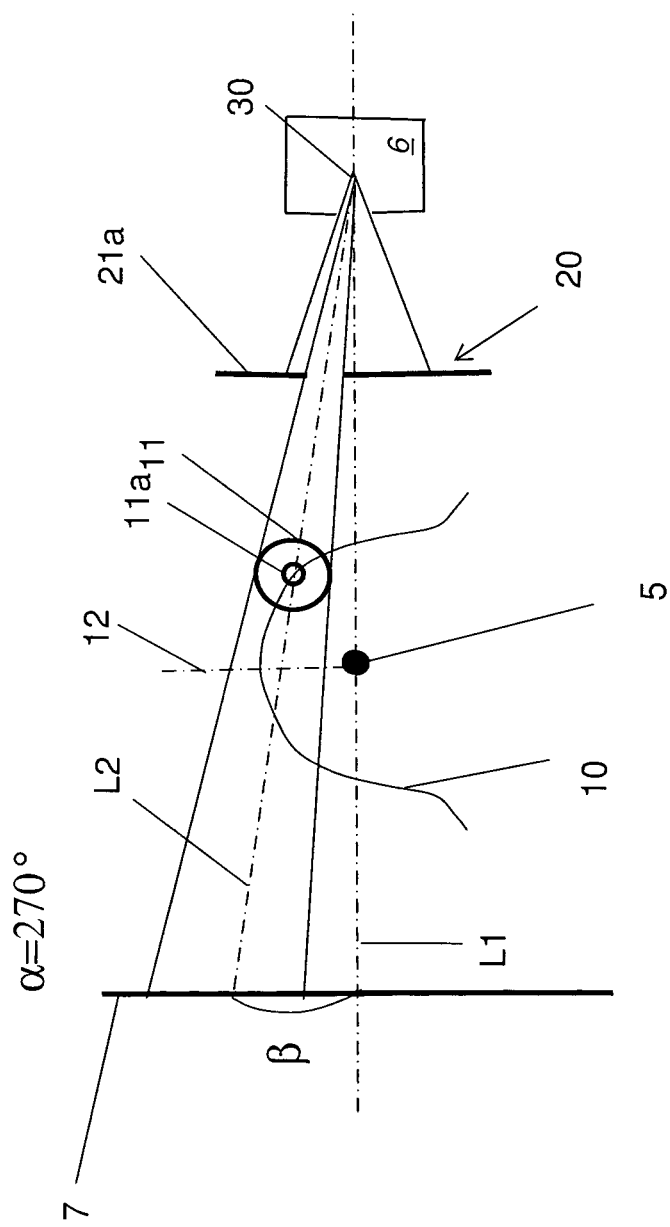

FIG. 4B shows a collimator 60 in an alternate embodiment of the present invention. A slit 63 provides the collimator opening, which is not adjustable in size. Motor 25 is coupled to collimator 60 for horizontal movement, as shown. According to the embodiment of the present invention using collimator 60, a single motor 25 is used for translating the plate provided with its opening slit, in place of paired blades 21a, 21b. Slit collimator 60 can be used in place of blade collimator 20 in embodiments shown subsequently. A single motor 25 can be used in a similar manner for translating a plate that is provided with slit 63 in place of the two blades 21b. Slit 63 can vary in dimensions, based on capabilities or constraints of the imaging system components. Other types of collimators are used in alternate embodiments of the present invention, such as those providing circular and elliptical apertures; these collimator types are similarly equipped to shift the central axis of the projected radiation beam away from the standard axis of line L1.

In some cases, the dentist needs information about only a small part of the dental arch 10, for example, from only two or three teeth. In such a case, a CT scan with a small field of view is performed, the x-ray beam being tightly collimated by collimator 20. The solution provided in embodiments of the present invention is advantaged for a number of reasons. First, the x-ray sensor 7 can be reduced in size and lower in price. Secondly, since this limited field of view requires only a small size x-ray beam that is collimated by collimator 20, the amount of ionizing radiation that is directed to the patient is reduced.

As noted earlier, one drawback with conventional CT apparatus relates to the need for precise 2D positioning of the axis of rotation 5, aligning axis 5 with center 11a, even where only a small portion of the dental arch 10 is to be imaged. Embodiments of the present invention relax this requirement, simplifying setup and use of the CT imaging apparatus 400, such as when only a limited-scan CT image is needed.

FIGS. 2A and 2B showed how lines L1 and L2 are collinear for conventional CBCT imaging. Line L1 passes through focal spot 30 of the x-ray source 6 and through the vertical projection of the axis 5. Line L2 indicates the center of the x-ray beam as it is directed through opening 23 of collimator 20 and, in the conventional arrangement, passes through the vertical projection of axis 5. Embodiments of the present invention allow these lines to be non-collinear and non-parallel and, instead, use the collimator 20 to control beam projection and centering at each imaging angle. At each angular position, angle α of the scan between the straight line L1 and the front-to-rear (e.g., anteroposterior) direction 12, motors 25 of collimator 20 (FIG. 4A) are energized to position the lateral blades 21a in such a way that center line L2 of the x-ray beam generated by focal spot 30 and passing through collimator 20 passes through center 11a of the region of interest 11, which need not coincide with the projection of axis 5. This behavior is shown at different angles in the sequence of FIGS. 5A-5E. In each case, the center of opening 23 of collimator 20 is not positioned on the straight line L1. Consequently, both straight lines L1 and L2 may not trace the same path as they do in conventional practice; instead, lines L1 and L2 are respectively non-parallel, at a non-zero angle β. At each image acquisition angle α in the FIGS. 5A-5E sequence, the rotation axis 5 lies outside the centered radiation beam. The accumulation of frames in an angle α angular range from 0° to 180° or from 0° to 360° gives the information needed for the complete reconstruction of the 3D matrix of absorption coefficients. The position of collimator blades 21a is sensed and is used for image capture and for x-ray sensor 7 positioning, as described in more detail subsequently. According to an embodiment of the present invention, motors 25 are stepping motors, allowing tracking information on blade positioning as part of actuation. Alternately, one or more sensors 46 (FIGS. 4A, 4B) provide the needed information on where one or both edges of the collimator opening 23 lie.

Figure 6:
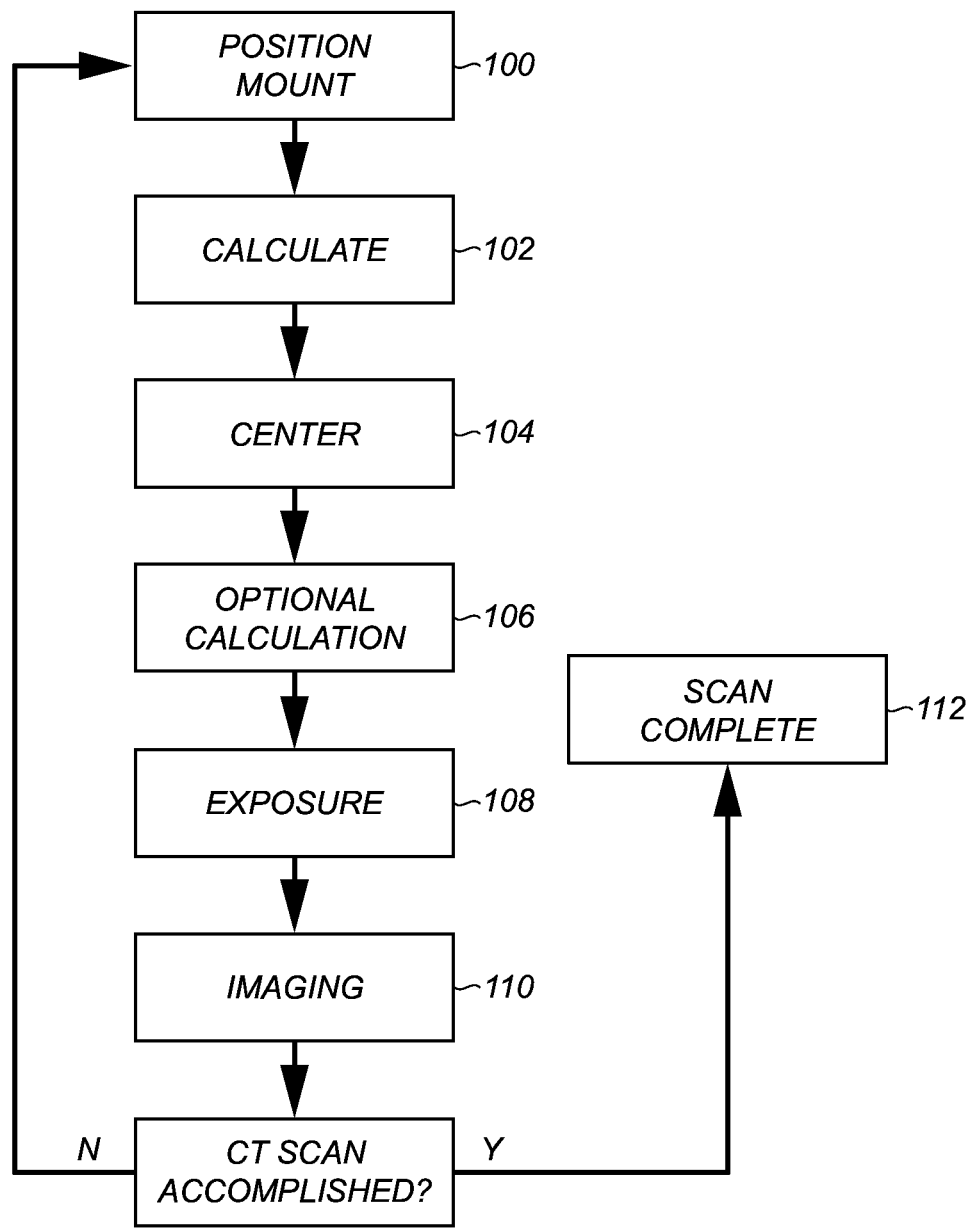
FIG. 6 is a logic flow diagram that lists the steps for obtaining a CT scan according to an embodiment of the present invention.

The complete scan is then performed following a succession of steps for an identified center 11a of region of interest 11, as outlined in the logic flow diagram of FIG. 6. At a mount positioning step 100, mount 4 is positioned at a predefined angle α position. As part of initial mount positioning step 100, optional motor 31 (FIG. 3) can be used to reposition mount 4 and thus axis of rotation 5 to a suitable angular position, as indicated by the technician or other operator. Motor 31 moves mount 4 to each angle α for imaging according to instructions entered by the operator, such as using computer unit 50 or using one or more controls 45 provided on the equipment for mount 4 positioning. According to an alternate embodiment of the present invention, motor 31 is responsive to operator movement and runs in an "assist" mode. In this mode, motor 31 is actuated as needed to shift the position of mount 4 based on sensing the direction in which an operator is manually pushing against or pulling mount 4. According to another alternate embodiment, an optional control 45 is used to actuate motor 31 to move mount 4 in a desired direction.

The position of region of interest 11 is also identified and stored by control software as prerequisite information or as part of an initial mount positioning step 100. Consistent with an embodiment of the present invention, region of interest 11 is defined in coordinate space, relative to the axis of rotation 5 as an origin or reference.

The coordinates of region of interest 11 are entered by target positioning, as described previously with reference to FIG. 1 or manually by the operator, such as at computer unit 50 (FIG. 3). According to an alternate embodiment, region of interest 11 is specified by identifying the specific teeth or other structures to be imaged as well indicating the relative size of the patient, or providing other information related to relative patient dimensions, or using a standard setup procedure that is suited to a child or adult patient size. Appropriate positioning of the patient and use of a template corresponding to standard patient dimensions provides a suitable estimate of the appropriate location of region of interest 11.

At a calculation step 102, processor 90 uses the position information for region of interest 11 and the detected, existing position of imaging components on mount 4 and executes control software instructions that calculate the desired position of lateral blades 21a for the new angular position of mount 4. At a collimator centering step 104, one or more of motors 25 of collimator 20 (FIG. 4A) are energized under control of the software executing on control logic processor 90 to position the collimator opening 23, such as positioning lateral blades 21a appropriately, so that the radiation beam through collimator 20 is centered about region of interest 11 with center 11a. As FIGS. 5A through 5E show, the positioning of the opening 23 of collimator 20 is recalculated for each angular position α at which an image is obtained. This calculation takes into account the relative angular displacement of region of interest 11 from axis 5 and adjusts collimator 20 so that radiation is centered about line L2, which is displaced by angle β from line L1. In embodiments that use the slit collimator 60 that is shown in FIG. 4B, slit 63 is correspondingly positioned so that radiation is centered about line L2. Other collimator embodiments perform similar centering of the collimator aperture.

Using a blade arrangement as shown in FIG. 4A, it is possible to adjust the boundaries of the radiation beam so that only a portion of the x-ray sensor 7 receives image content. Using the slit arrangement of FIG. 4B, boundaries of the slit are fixed; similarly, only a portion of the x-ray sensor 7 receives image content with the slit collimator configuration. As is shown in the sequence of FIGS. 5A through 5E, the portion of the x-ray sensor 7 that obtains the image data varies with either blade or slit collimators, depending on rotation angle α. The partial imaged area of x-ray sensor 7 can vary from one angular setting to the next. Using the basic sequence described herein, it is straightforward to determine which pixels of x-ray sensor 7 are affected at each angular position. By reading only irradiated pixels and ignoring the larger body of repetitive pixel values that have no diagnostic utility, embodiments of the present invention help to reduce the overall amount of data needed for effective CT imaging of teeth and other structures. For example, the imaged portion of x-ray sensor 7 can require less than 70% of the available pixels, such as less than 60%, less than 50%, or less than 40%, for example. It should also be noted that for embodiments in which the size of the collimator opening is adjustable, the corresponding area of irradiated pixels can be varied according to the mount rotation angle α.

At an optional calculation step 106, the system calculates which pixels of x-ray sensor 7 are to be read at the given angular position. At an exposure step 108, the x-ray source is energized and at an imaging step 110 selected pixels are read. Once the CT scan is completed, at a step 112, the processor calculates a three dimensional matrix of x-ray absorption coefficients from the obtained image. A 3-dimensional (3D) matrix of a region of interest can then be obtained on the basis of a suitable number of image frames.

Pixel selection relative to the given angular position of the mount and the collimator position and opening location can be performed in a number of ways and can vary with rotation angle. At each angular position of mount 4, lines L1 and L2 are directed from focal spot 30 at a corresponding angle β, based on the relative distance of region of the center 11a of the region of interest 11 from axis of rotation 5 at that mount angle. Because the distance between focal spot 30 and x-ray sensor 7 is constant and line L1 through focal spot 30 and axis 5 is normal to the collimator 20 and to the surface of x-ray sensor 7, the center position at which line L2 intersects the x-ray sensor 7 relative to line L1 is proportional to sin p. Further, the position of collimator 20 from the focal spot 30 is also fixed. Thus, the width of the radiation beam, centered at line L2, can be computed in a straightforward manner, once the size of the collimator aperture, that is, the relative location of collimator edges away from line L1 is known. The corresponding edges of the imaged area on x-ray sensor 7 are then simply computed using straightforward geometric relationships.

Providing sensor 70 using CMOS or TFT sensor technology allows selection of pixels to be read by well known pixel addressing techniques. In conventional imaging apparatus, pixels can be selected to change the size of the image according to the size of region of interest 11. According to an embodiment of the present invention, this selection of pixels is used essentially to selectively read the pixels corresponding to the area of the sensor that the collimated x-ray beam impinges upon.

Advantageously, the extra-oral dental imaging device according to embodiments of the present invention allows the 3D matrix of absorption coefficients of any region of interest of the patient's mouth to be obtained without the need for precisely positioning axis 5 so that it extends through center 11a during the imaging sequence, thus making it unnecessary to require motors 31 and 32 as in the FIG. 1 embodiment.

Figure 7A:
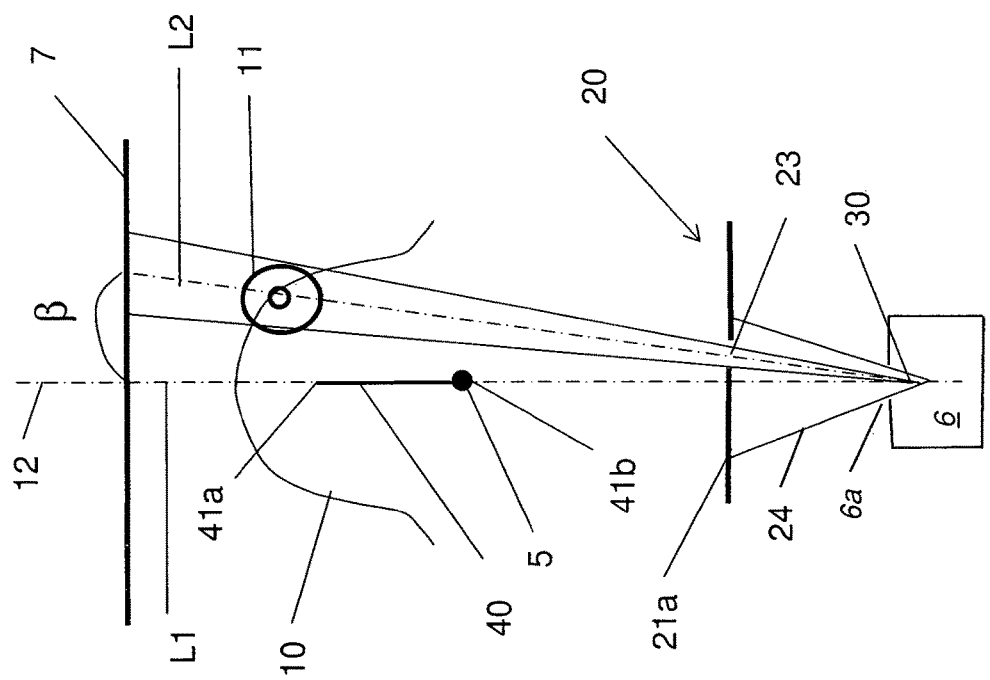
FIGS. 7A-7D are top views that show different angles in an imaging sequence using the adjustable collimator for beam direction according to an alternate embodiment of the present invention.
Figure 7B:
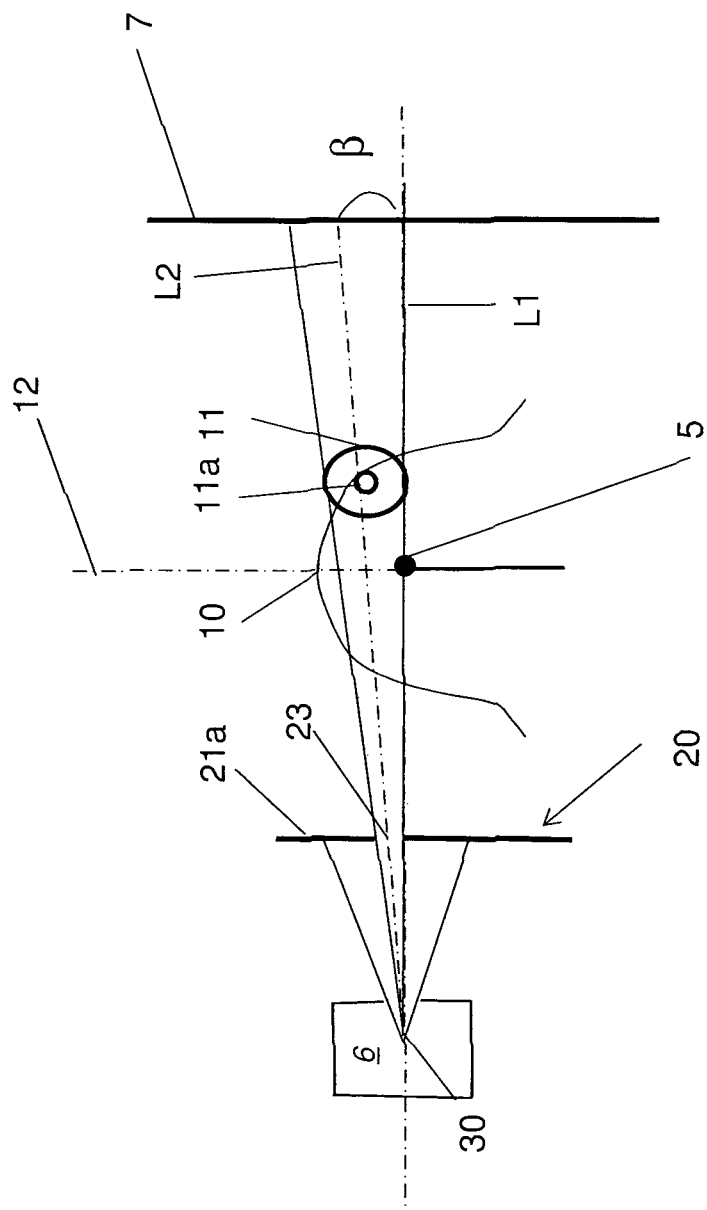
Figure 7C:
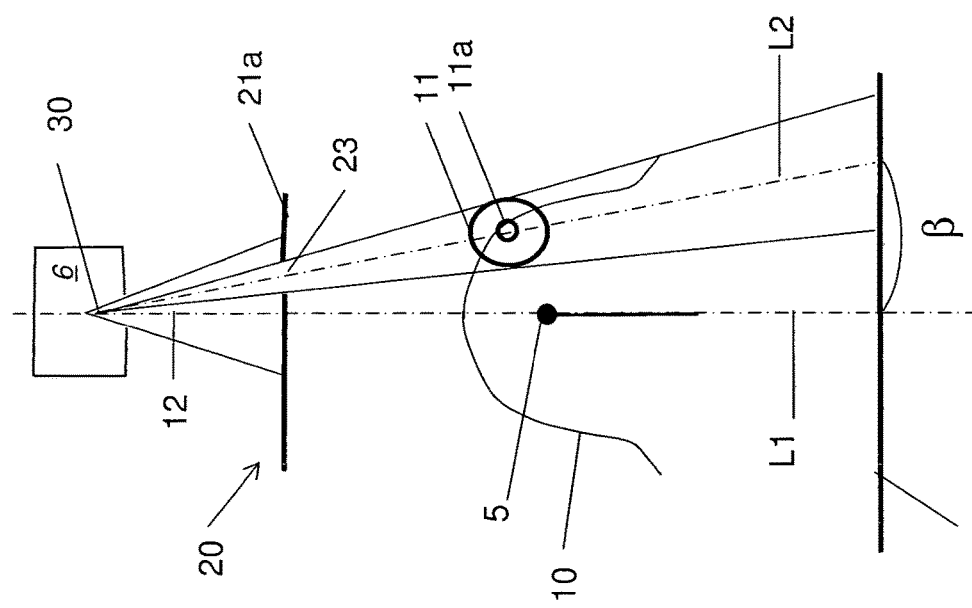
Figure 7D:
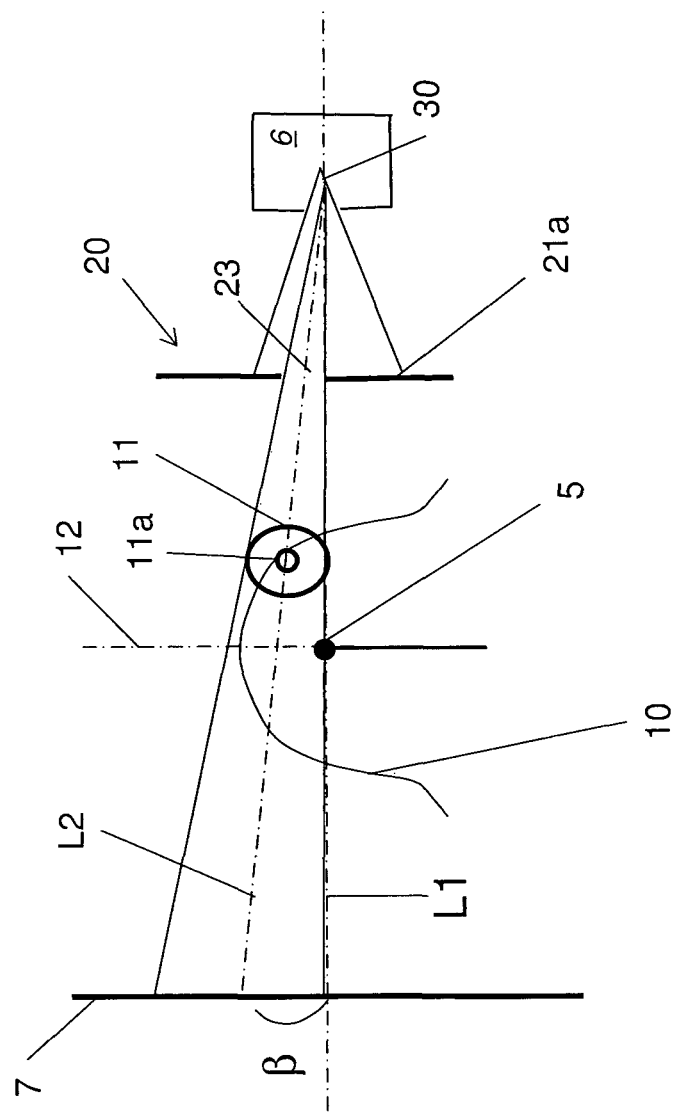
Figure 8A:
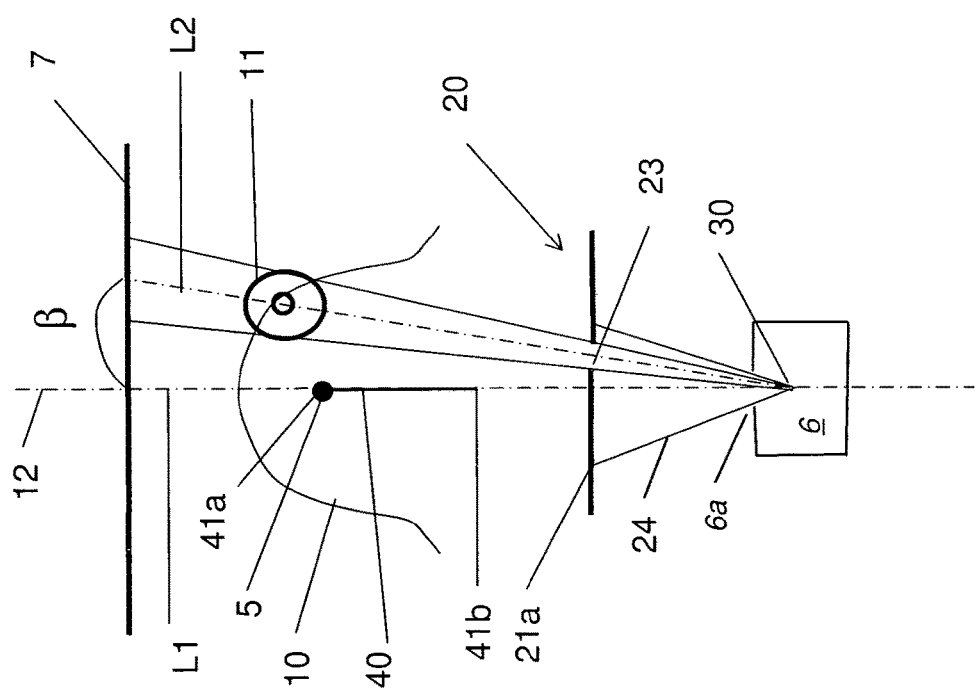
Figure 8B:
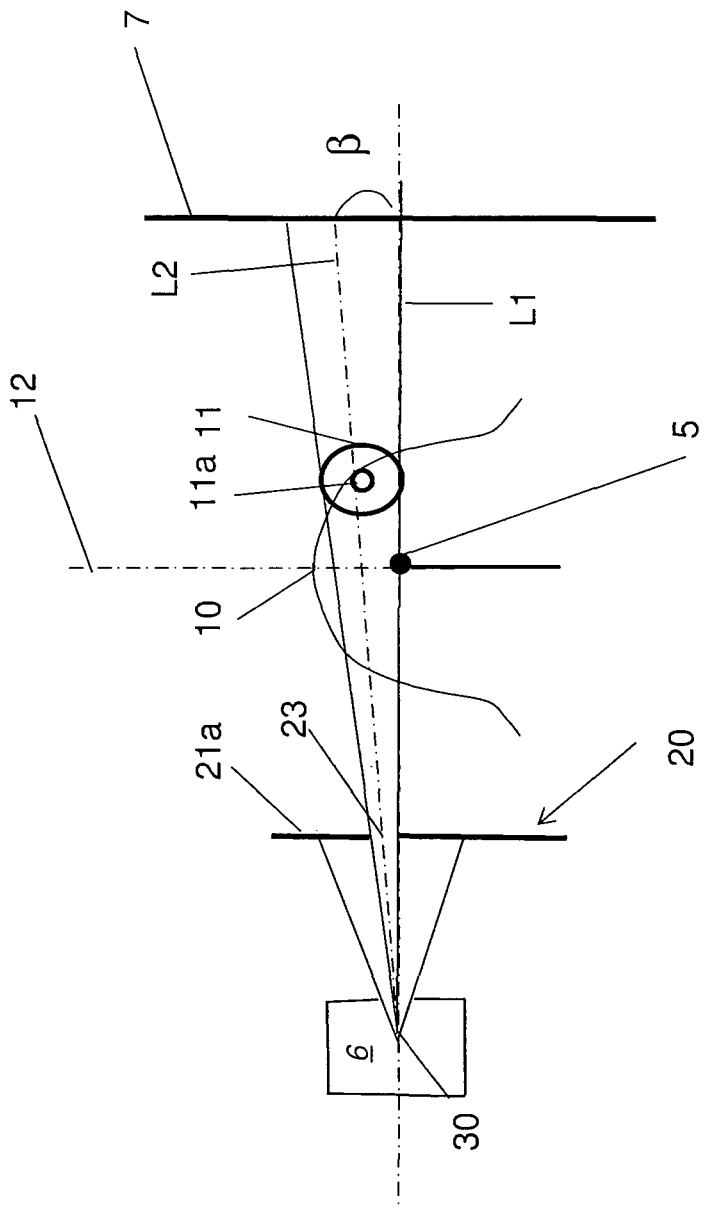
Figure 8D:
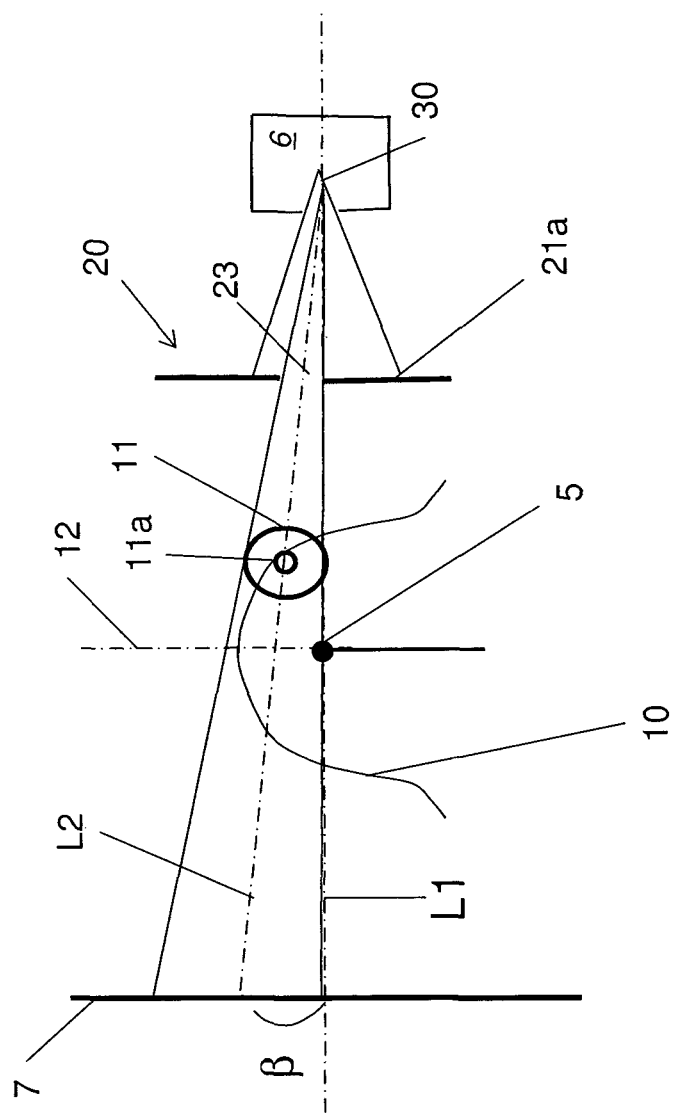

An alternate embodiment of the present invention is shown in the sequence of FIGS. 7A through 7D. Here, axis 5 can be displaced along one direction. A single motor 31 is mounted in horizontal arm 2 as was shown in FIG. 1. Motor 31 is energizable to provide translational movement of axis 5 along a single direction, preferably in the anteroposterior direction 12. As shown in FIG. 7A, axis 5 can then be positioned in any location between two extreme positions 41a and 41b of a segment 40 that corresponds to the extent of movement provided by motor 31. For each value of angle α between the line L1 and the anteroposterior direction 12, that is, for each angular position that is used for imaging, the position of axis 5 on segment 40 is chosen in such a way that the area of the x-ray sensor 7 that is subtended by angle β is reduced to obtain only useful image data for the region of interest 11 or is, more generally, chosen to have a position that simplifies acquisition of the corresponding image, such as by positioning axis 5 or x-ray source 6 as close as possible to center 11a of region of interest 11, for example.

Another alternate embodiment of the present invention, offering the capability for improved resolution over embodiments described previously, is shown in the sequence of FIGS. 8A through 8D. Here, axis 5 can be displaced along one direction. For each value of angle α between the line L1 and the anteroposterior direction 12, that is, for each angular position, the position of axis 5 on segment 40 is chosen in such a way that x-ray source 6 is as close as possible to region of interest 11. With this relationship, the projection of the x-rayed object on x-ray sensor 7 is as large as possible, helping to increase image resolution.

Figure 9:
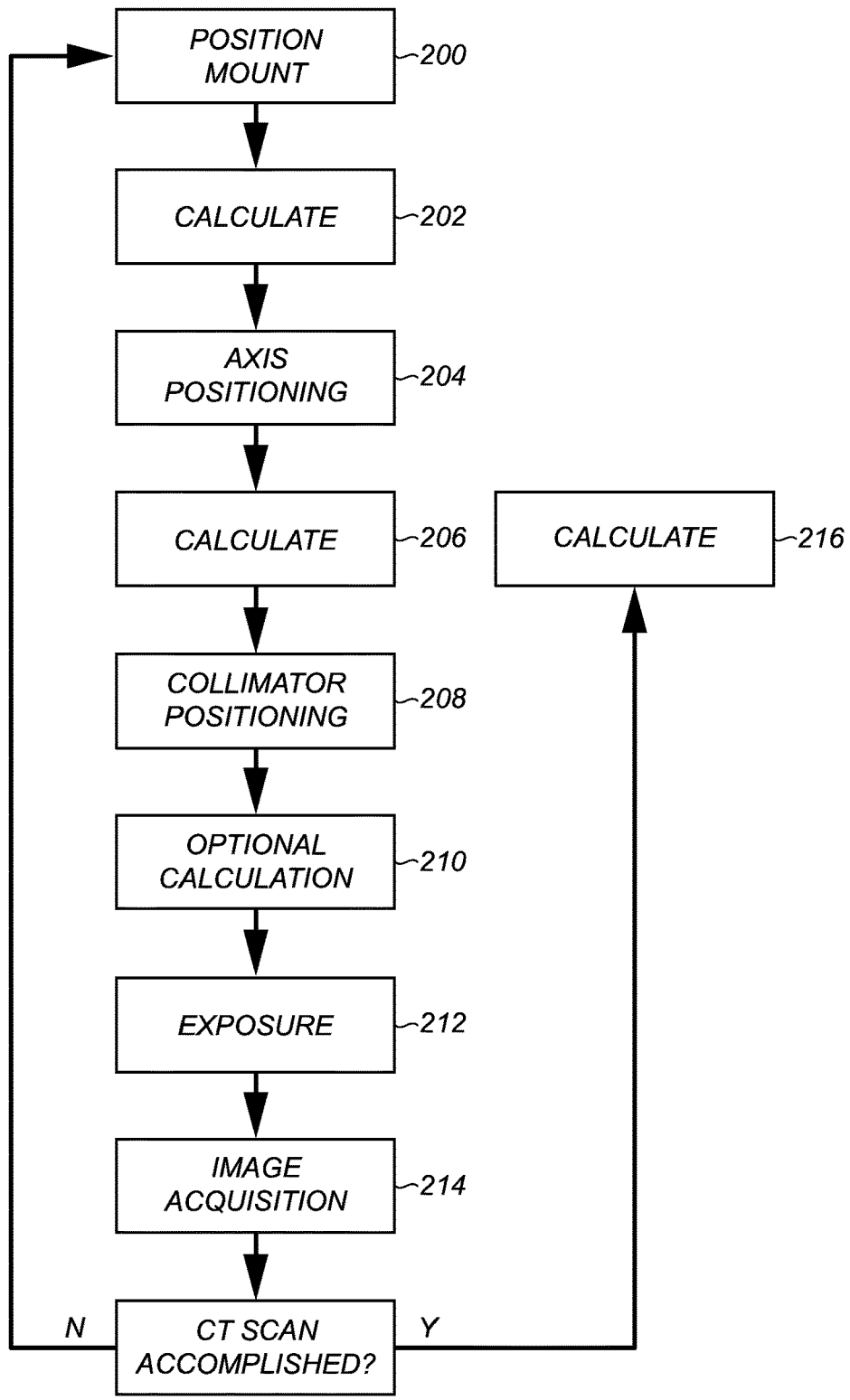
FIG. 9 is a logic flow diagram that lists the steps for obtaining a CT scan according to an alternate embodiment of the present invention.

The complete scan for the alternate embodiments of FIGS. 7A-7D and 8A-8D is then performed following the succession of steps given in FIG. 9. In a positioning step 200, mount 4 is positioned at a predefined angle α position about the axis. In a calculation step 202, the processor calculates the most convenient position of axis 5 along segment 40, as described with reference to FIG. 7A. In an axis positioning step 204, motor 31 positions the axis in the calculated position. In a calculation step 206, the processor calculates the position of lateral blades 21a for the new angular position of mount 4. In a collimator positioning step 208, motors 25 of collimator 20 position lateral blades 21a. In an optional calculation step 210, the processor calculates which pixels of x-ray sensor 7 are to be read at the given angular position. In an exposure step 212, the x-ray source is energized and the image obtained in an image acquisition step 214, with selected pixels read. At completion of the CT scanning to obtain each image at a different angular position using these steps, the processor calculates a three dimensional matrix of x-ray absorption coefficients in a calculation step 216.

In the embodiment described with reference to FIGS. 7A-7D, patient support, positioning apparatus 14 of apparatus 300 is designed so that segment 40 coincides with the plane of symmetry of the patient and so that one extremity position 41b of the segment is in a known relationship relative to the anatomy of the patient and is, for example at the vertical position, or height position, of the patient's mouth. The same arrangement of computer unit 50 components and manipulation of target 53 position to define the location of axis 5, described previously with respect to FIG. 3, also apply for the alternate embodiments shown in FIGS. 7A-7D and 8A-8D.

In the embodiments described, the region of interest can include a region of one single dental arch, either maxillae or mandible, or the opposite region of both dental arches, depending on the position of the collimator blades 21a or 21b defining the vertical width of collimator 20 (FIG. 4A).

Processing for generating the extra-oral imaging data to provide a volume image can be executed on control logic processor 90, which can be a dedicated microprocessor or host computer associated with the CT imaging apparatus, or on some other computer processing system, including a remotely networked processor, for example. It can be appreciated that functions such as control of the rotational position of the imaging hardware, image acquisition, image data processing, and generation and display of volume image data can be performed from a single computer system or using a group or network of computers and host processors that interact with each other to control system components and to provide these functions.

Among its functions for control and image acquisition, control logic processor 90 (FIG. 3) stores and executes control software that generates, for one or more rotation positions of the rotatable mount, a signal for collimator adjustment for centering the beam on the region of interest.

Figure 10:
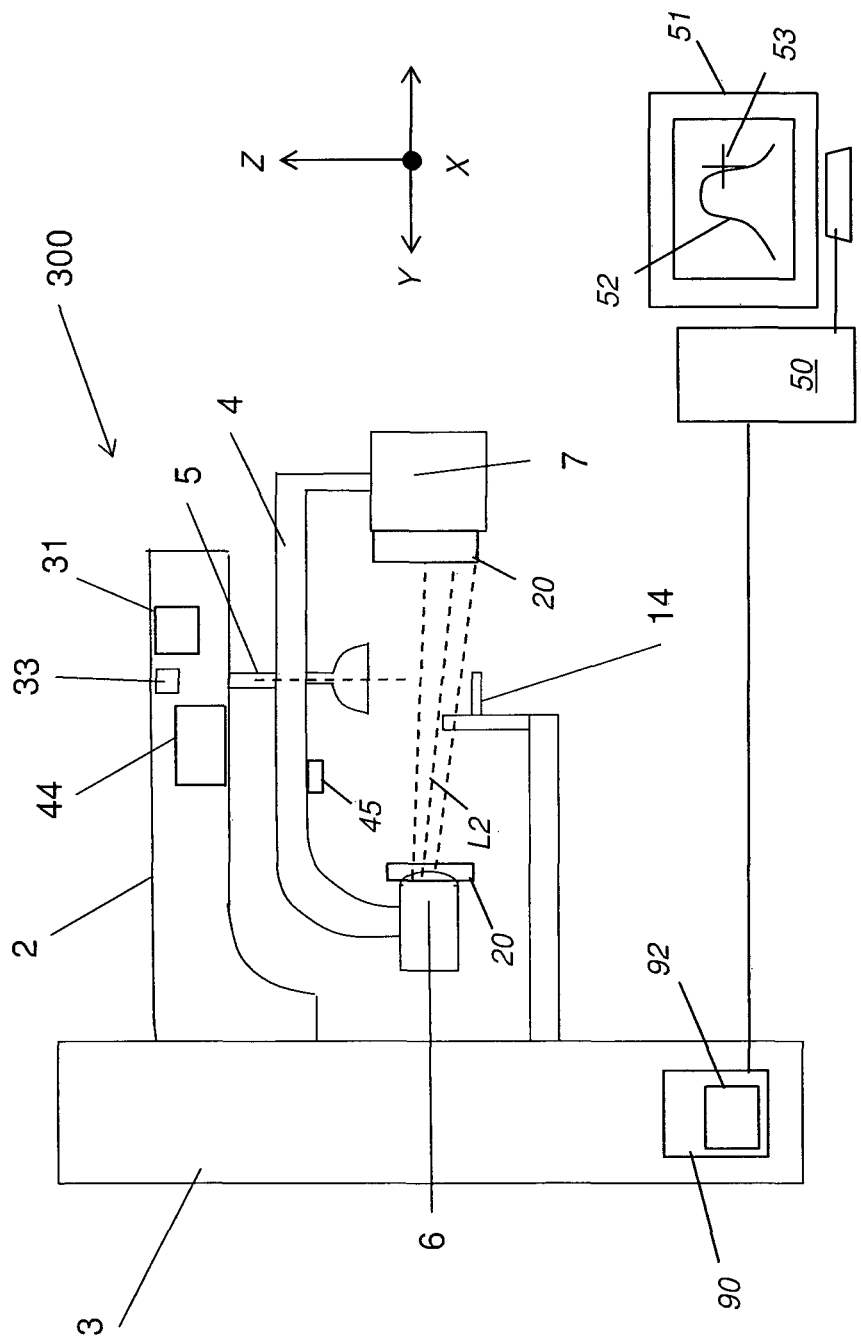
FIG. 10 is a schematic diagram that shows the use of a blade collimator for diverting the X-ray beam in the vertical direction.

FIGS. 5A-5E, 7A-7D, and 8A-8D show displacement of the center of the emitted radiation along a horizontal direction, that is, relative to the plane of the page as viewed in these figures. It is to be observed that some amount of vertical displacement, out of the plane of the page, can alternately be provided in addition where collimator 20 allows vertical beam adjustment, as shown in the example of FIG. 4A. Horizontal blades 21*b* can be positioned suitably for this purpose, so that the x-ray beam is directed from an angle, with corresponding image data obtained at a vertical position on x-ray sensor 7. The schematic diagram of FIG. 10 shows the use of collimator 20 in diverting the X-ray beam along line L2 in the vertical (z) direction. Referring to FIG. 9, calculation step 206 optionally includes the added calculations for vertical adjustment of the opening of collimator 20 for this purpose. Vertical blades 21*b* are then moved as part of positioning step 208. It should be noted that the capability to adjust the angle of the emitted beam with respect to vertical gives a measure of added control to the standard height adjustment that is provided for arm 2 and mount 4.

It should be noted that in the various embodiments of the CT imaging apparatus shown herein, wherein lines L1 and L2 follow separate paths, the x-ray radiation can be incident on x-ray sensor 7 at slightly larger angles than with conventional imaging wherein lines L1 and L2 follow the same path, as described previously with reference to FIGS. 2A and 2B. According to an alternate embodiment of the present invention, image processing algorithms performed by control logic processor 90, by remote computer 50, or by some other computer determine which pixels provide image data at a particular rotation angle α and compensate for this slight difference in angular spread.

The digital x-ray sensor 7 that is used for CT imaging is a costly component. The larger the sensor, the higher the cost. As noted with reference to embodiments in FIGS. 5A-5D and following, only a portion of the x-ray sensor 7 is needed for obtaining image data at each angular position α. This means that a considerable amount of the imageable area is wasted when obtaining the series of 2-D images used for CT image reconstruction. Referring to FIGS. 11A-11D, there is shown an embodiment of the present invention that addresses the cost problem by employing a smaller x-ray sensor 70 that is moved along a track 72. One or more motors 74 and 76 are provided to urge x-ray sensor 70 along track 72 for obtaining the image at each rotation angle α.

For moving x-ray sensor 70 to the various angular positions in the FIG. 11A-11D sequence, the same considerations and calculations described previously for reading only the imaged pixels apply. Instead of using only a small portion of the image area of the sensor, embodiments of the present invention allow more efficient use of the sensor, translating the sensor to a suitable position for each imaging angle. Control logic processor 90 coordinates positioning of x-ray sensor 70 along track 72 according to the mount angle α and the detected coordinates for opening 23 of collimator 20. According to an alternate embodiment of the present invention, a single motor is actuable to urge x-ray sensor 70 to each position along track 72. Various arrangements of gears or belts can be used for moving the x-ray sensor 70.

Figure 11A:
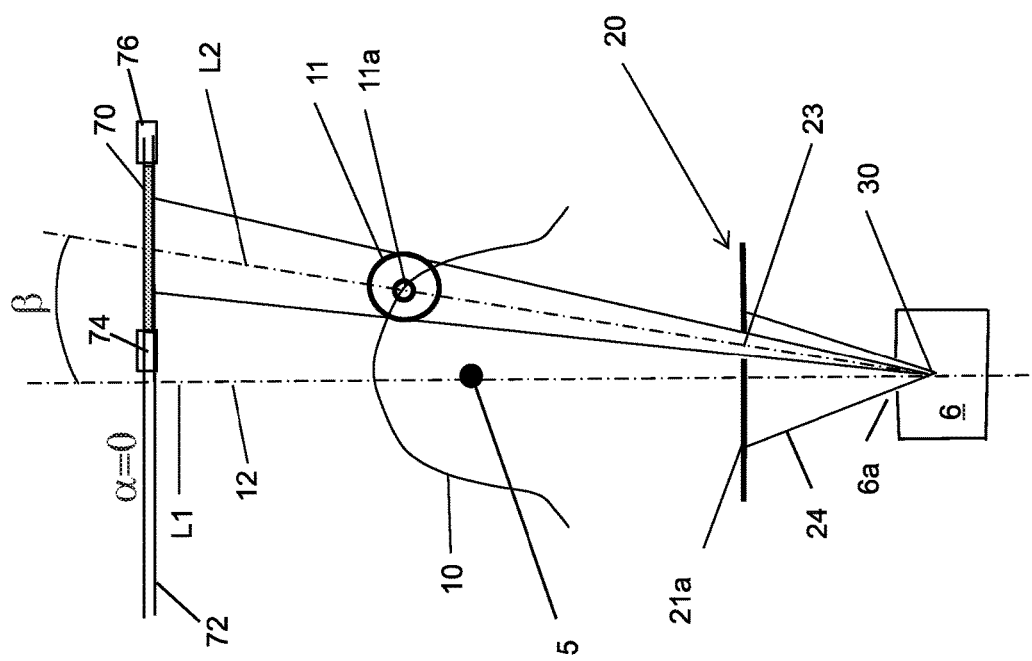
FIGS. 11A-11D are top views that show different angles in an imaging sequence using the adjustable collimator for beam direction along with a smaller sensor that is moved along a track according to an embodiment of the present invention.
Figure 11B:
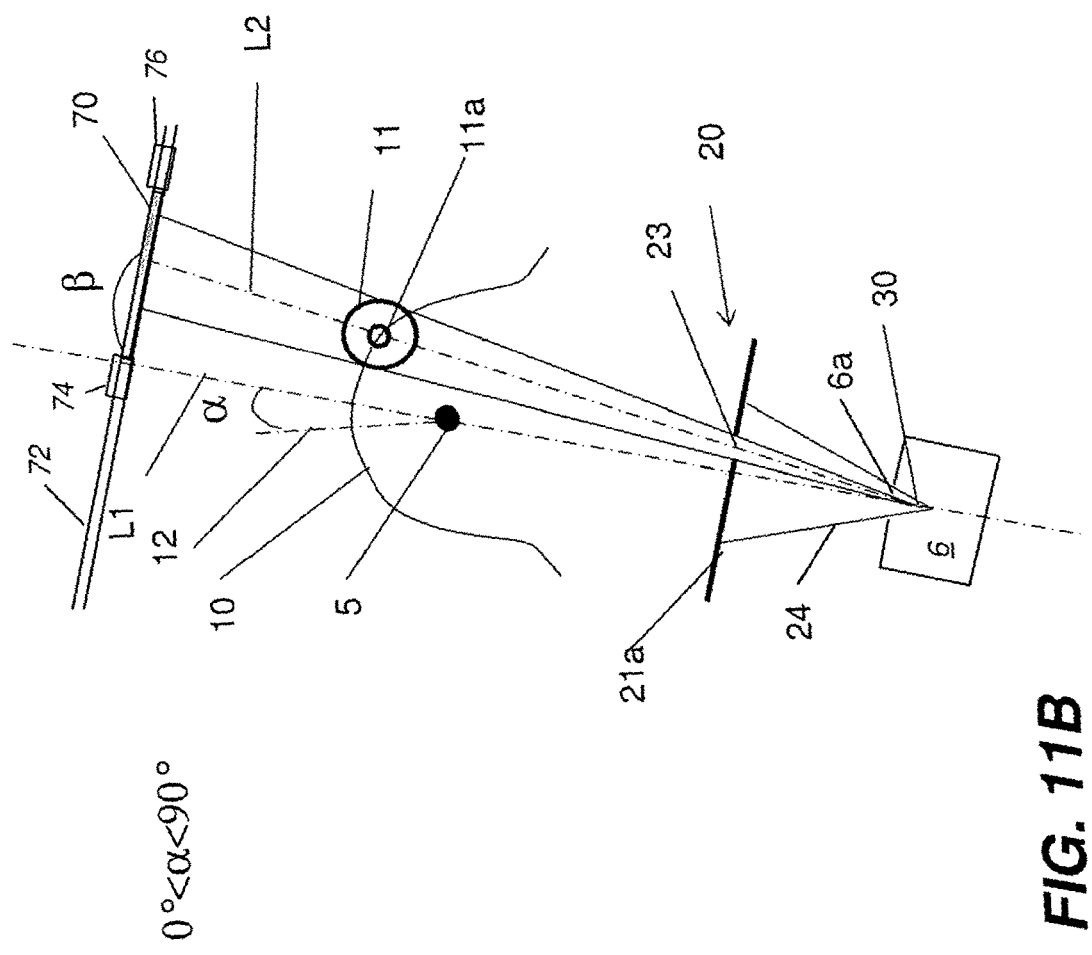
Figure 11C:
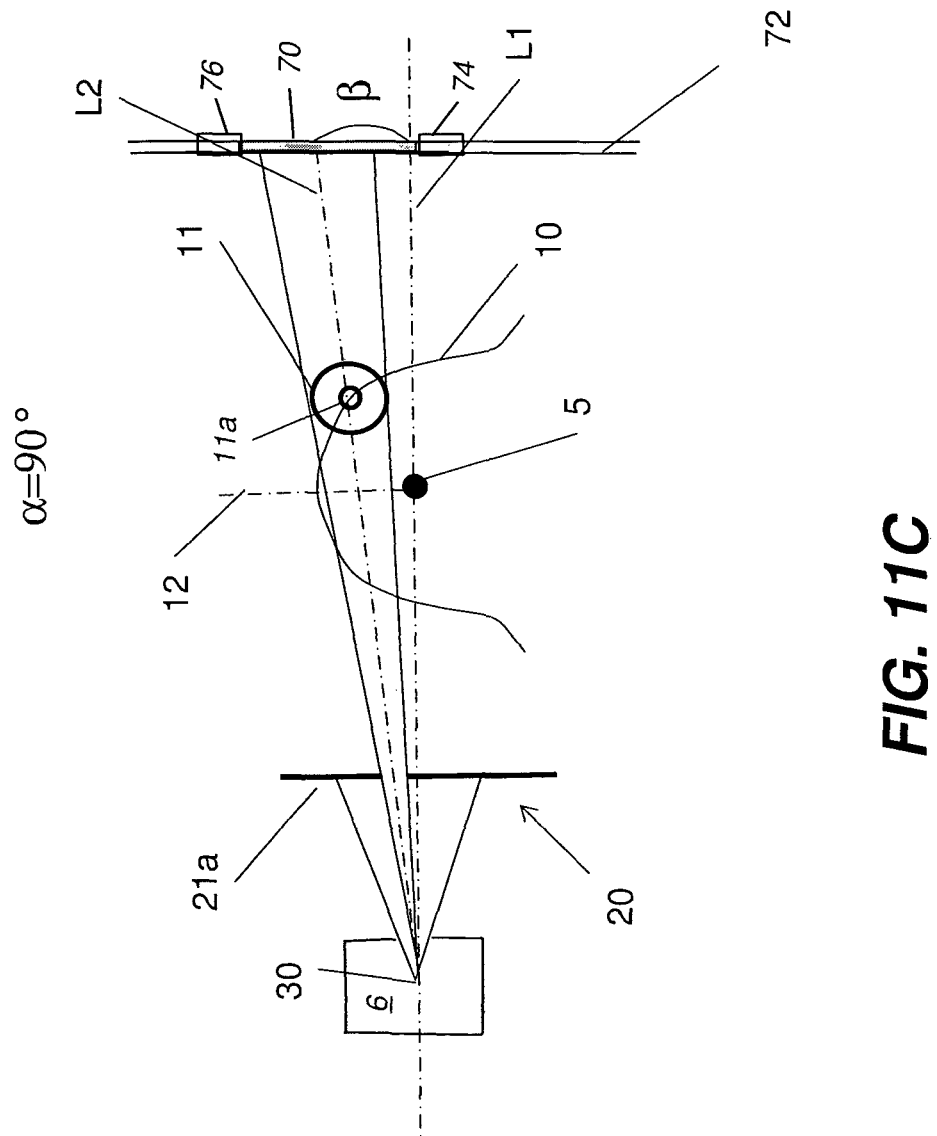
Figure 11D:
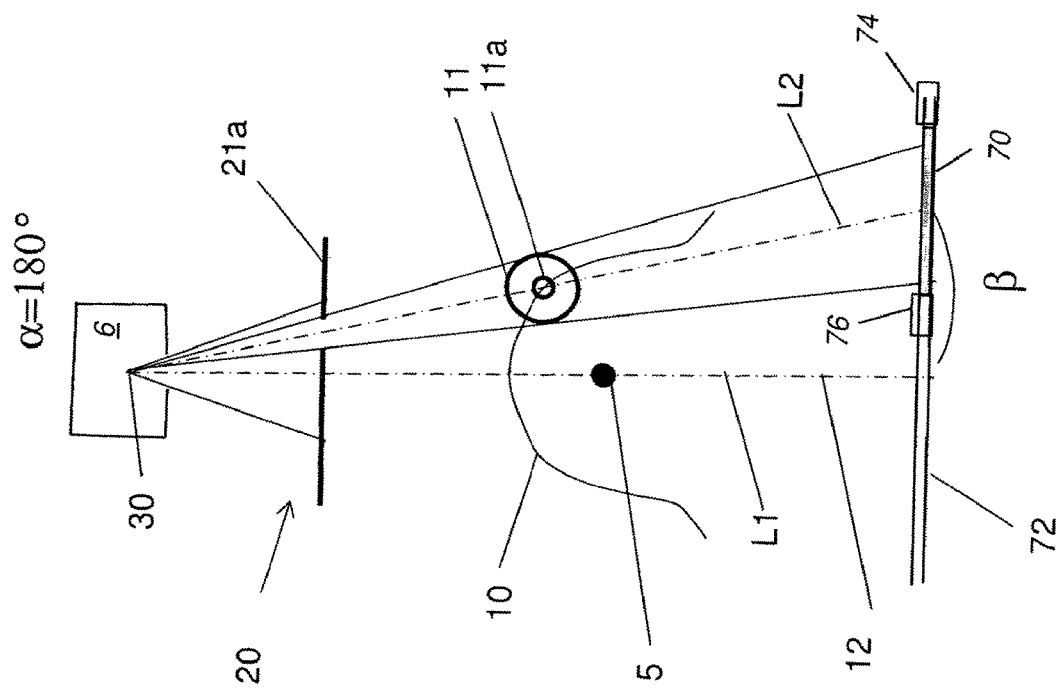
Figure 11E:
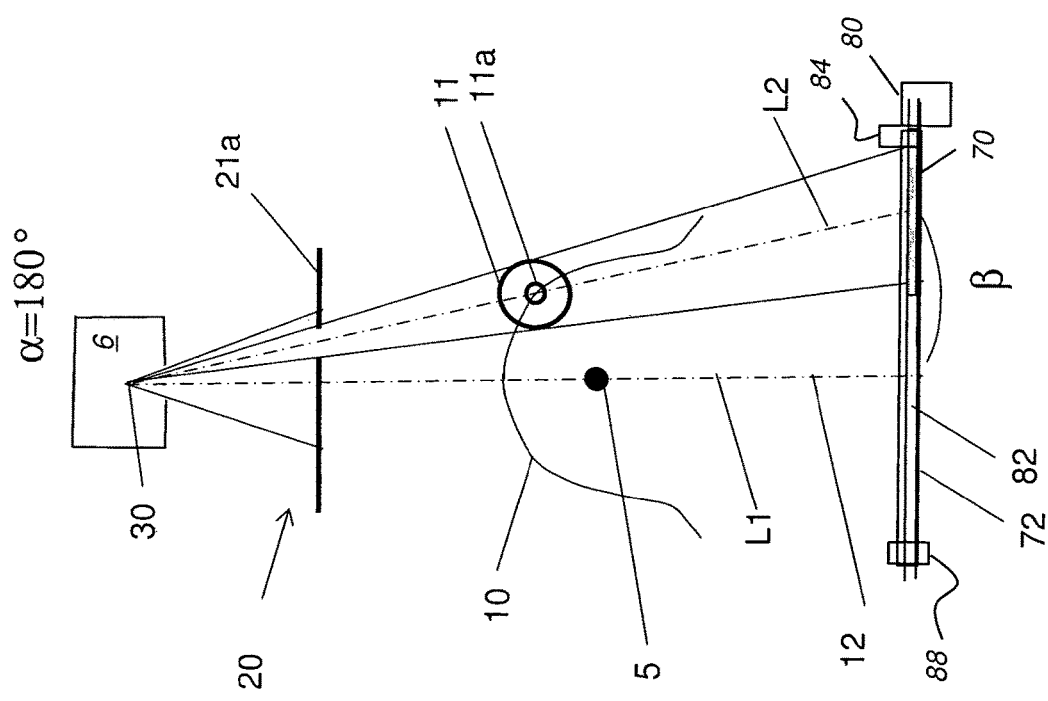
FIG. 11E is a schematic diagram showing an alternate embodiment for movement of the x-ray sensor along a track.

Techniques for providing sliding movement of an x-ray sensor on a panel are well-known in the art of standard linear tomography. In conventional devices, both the sensor and the source translate in parallel, moving either in the same direction or in opposite directions. According to an alternate embodiment of the present invention as shown in FIG. 11E, a stepping motor 80 actuates a worm screw device 82 (a so-called endless screw) that urges x-ray sensor 70 along track 72. The use of a stepping motor allows a precise determination and control of the actual position of x-ray sensor 70 along the track. Two motion sensors 84, 88 are positioned at both extremities of track 72 to determine the precise reference points for the start and the end of the length of stroke of x-ray sensor 70. These motion sensors 84, 88 can send a signal to control logic processor 90 to stop the displacement of x-ray sensor 70 when it reaches an end of the stroke. Alternately, the position of x-ray sensor 70 can also be determined using a resistive track 72: the measured electric resistance from resistive track 72 is proportional to or is a function of the distance between a point of x-ray sensor 70 and a reference point on the resistive track 72.

Consistent with an embodiment of the present invention, a computer or other logic processor executes a program with stored instructions that control aspects of apparatus operation for obtaining an image and, optionally, also process image data accessed from the x-ray sensor or stored in an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise obtaining and processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types. Computer-accessible memory of various types is provided on different components throughout the system for storing, processing, transferring, and displaying data, and for other functions.

In the context of the present disclosure, the terms "operator", and "user" are considered to be equivalent and refer to the technician or practitioner or other person who sets up and initializes a partial CT imaging scan.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An apparatus for computed tomography imaging of a patient, comprising:
   a rotatable mount that is actuable to rotate about a rotation axis, the rotatable mount comprising:
      an x-ray source disposed to direct, at each of a plurality of angular positions of the rotatable mount about the rotation axis during a computed tomography scan, a radiation beam through an imaging area,
      a collimator disposed in front of the x-ray source,
      a detector track positioned in opposition to the x-ray source across the imaging area,
      a detector mounted at the detector track, wherein the detector is of a smaller size that is irradiated with the radiation beam through the collimator and the imaging area, and
      an actuator to move the detector to a plurality of different positions along the detector track, and wherein the detector is moved by the actuator along the detector track to the plurality of different positions along the detector track to form image data including a frame image at each of the plurality of different positions along the detector track according to the radiation beam during the computed tomography scan;
   a patient positioning apparatus for positioning relative to the rotation axis;
   a control logic processor coupled to the x-ray source, the collimator, the actuator, and the rotatable mount that controls rotation of the rotatable mount and an opening of the collimator, wherein the control logic processor controls a position of the detector along the detector track according to a mount angle of the rotatable mount and detected coordinates for the opening of the collimator at said each of the plurality of angular positions to acquire the image data from the detector at said each of the plurality of angular positions about the rotation axis while centering the radiation beam through the opening of the collimator, at said each of the plurality of angular positions, on a region of interest that is spaced apart from the rotation axis.

2. A method for computed tomography imaging of a patient, comprising:
   providing a rotatable mount that is actuable to rotate about a rotation axis and the rotatable mount comprises, in opposition, an x-ray source and an x-ray detector for obtaining a plurality of frame images;
   directing, at each of a plurality of angular positions of the rotatable mount about the rotation axis, a radiation beam from the x-ray source through an imaging area;
   providing a patient positioning apparatus for positioning relative to the rotation axis;
   providing a collimator between the x-ray source and the imaging area;
   directing, at said each of the plurality of angular positions of the rotatable mount about the rotation axis, the radiation beam from the x-ray source through the collimator and the imaging area, wherein the x-ray detector is of a smaller size that is irradiated with the radiation beam through the collimator and the imaging area;
   moving the collimator to direct the radiation beam, at said each of the plurality of angular positions, toward a region of interest that is spaced apart from the rotation axis; and
   moving the x-ray detector to a plurality of different positions along a detector track according to a mount angle of the rotatable mount at said each of the plurality of angular positions and detected coordinates for an opening of the collimator at said each of the plurality of angular positions; and moving the x-ray detector to form image data including a frame image at each of the plurality of different positions along the detector track according to the radiation beam during a computed tomography scan, wherein the x-ray detector moves in opposite directions along the detector track during the computed tomography scan.

3. A method for computed tomography imaging of a patient, comprising:
   providing a rotatable mount that is actuable to rotate about a rotation axis and the rotatable mount comprises, at opposing ends, an x-ray source having a collimator and an x-ray detector for obtaining a plurality of frame images, wherein the x-ray source is disposed to direct a radiation beam through the patient and toward the x-ray detector;

accessing a region of interest of the patient, the region of interest having a center that is spaced apart from the rotation axis;

positioning the rotatable mount at a first angular position;

calculating the position of a center of an opening of the collimator at the first angular position for centering a radiation beam about the center of the region of interest;

acquiring a frame image at the first angular position;

rotating the rotatable mount to at least one second angular position;

changing the position of the center of the opening of the collimator at the at least one second angular position for centering a radiation beam about the center of the region of interest;

acquiring a frame image at the at least one second angular position;

forming a volume image according to at least image data acquired at the first angular position and the at least one second angular position; and displaying, transmitting, or storing the volume image;

changing the position of the opening of the collimator relative to a vertical direction; and storing one or more coordinates that identify the region of interest having the center that is spaced apart from the rotation axis.

4. The method of claim 3, wherein
the position of the rotation axis further depends on the angular position of the rotatable mount.

5. The method of claim 3, wherein
identifying the region of interest comprises adjusting a target on a display screen.

6. The method of claim 3, wherein the center of the region of interest is spaced apart from the rotation axis, wherein, for at least one of the first angular position and the second angular position, the rotation axis lies outside the centered radiation beam.

* * * * *